(12) United States Patent
Smith et al.

(10) Patent No.: US 11,226,336 B2
(45) Date of Patent: Jan. 18, 2022

(54) COMPACT AND HOMOGENEOUS QUANTUM DOTS AND METHODS OF MAKING THE SAME

(71) Applicant: The Board of Trustees of the University of Illinois, Urbana, IL (US)

(72) Inventors: Andrew M. Smith, Savoy, IL (US); Chunlai Tu, Urbana, IL (US); Liang Ma, Urbana, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 452 days.

(21) Appl. No.: 15/658,485

(22) Filed: Jul. 25, 2017

(65) Prior Publication Data
US 2020/0025772 A1    Jan. 23, 2020

Related U.S. Application Data

(60) Provisional application No. 62/366,303, filed on Jul. 25, 2016.

(51) Int. Cl.
| | |
|---|---|
| *G01N 33/58* | (2006.01) |
| *G01N 33/533* | (2006.01) |
| *B82Y 15/00* | (2011.01) |
| *C07K 2/00* | (2006.01) |
| *C01B 19/00* | (2006.01) |
| *C07K 16/18* | (2006.01) |
| *G01N 33/543* | (2006.01) |
| *B82Y 5/00* | (2011.01) |
| *B82Y 40/00* | (2011.01) |

(52) U.S. Cl.
CPC ......... *G01N 33/588* (2013.01); *C01B 19/007* (2013.01); *C07K 2/00* (2013.01); *C07K 16/18* (2013.01); *G01N 33/533* (2013.01); *G01N 33/54346* (2013.01); *G01N 33/587* (2013.01); *B82Y 5/00* (2013.01); *B82Y 15/00* (2013.01); *B82Y 40/00* (2013.01); *C01P 2002/84* (2013.01); *C01P 2002/86* (2013.01); *C01P 2004/64* (2013.01); *C07K 2317/569* (2013.01); *C07K 2319/21* (2013.01)

(58) Field of Classification Search
CPC ........... G01N 33/588; G01N 33/54346; G01N 33/587; G01N 33/533; C01B 19/007; C07K 16/18; C07K 2/00; C07K 2319/21; C07K 2317/569; B82Y 5/00; B82Y 15/00; B82Y 40/00; C01P 2002/84; C01P 2002/86; C01P 2004/64
See application file for complete search history.

(56) References Cited

U.S. PATENT DOCUMENTS

2011/0260111 A1* 10/2011 Nie ................... C01B 19/007
                                                                        252/301.36

OTHER PUBLICATIONS

Zhang et al. ("Click-Functionalized Compact Quantum Dots Protected by Multidentate-Imidazole Ligands: Conjugation-Ready Nanotags for Living-Virus Labeling and Imaging", J. Am. Chem. Soc. vol. 134, pp. 8388-8391, published May 8, 2012) (Year: 2012).*
Smith et al., Adv. Drug Deliv. Rev. 60, 1226-1240 (2008).
So et al., Nat. Biotechnol. 24 (2006), pp. 339-343.
Murray et. al. IBM J. Res. Dev. 2001, 45, 47-56.
Gujraty et. al. Polym. Sci., Part A: Polym. Chem. 2008, 46, 7249-7257.
Lim et. al., Nat. Commun. 2015, 6, 8210.
Nag et. al., J. Am. Chem. Soc 2011, 133; 10612-10620.
Segur and Oberstar, Ind. Eng. Chem. Res. 1951, 43; 2117-2120.

* cited by examiner

*Primary Examiner* — Tracy Vivlemore
*Assistant Examiner* — Nam P Nguyen
(74) *Attorney, Agent, or Firm* — Dilworth IP, LLC

(57) ABSTRACT

The present disclosure provides quantum dots and methods of making the quantum dots comprising a substantially homogeneous population of monomeric nanocrystals, of a very small size, about 7 nm to about 12 nm in diameter. The method comprises mixing a nanocrystal coated with weakly binding ligands or ions with a polymer in a solution and incubating at a temperature greater than about 100° C., thereby forming a quantum dot having a substantially homogenous population of monomeric nanocrystals. The quantum dots can be further conjugated to bioaffinity molecules, enabling broad utilization of compact, biofunctional quantum dots for studying crowded macromolecular environments.

11 Claims, 11 Drawing Sheets
Specification includes a Sequence Listing.

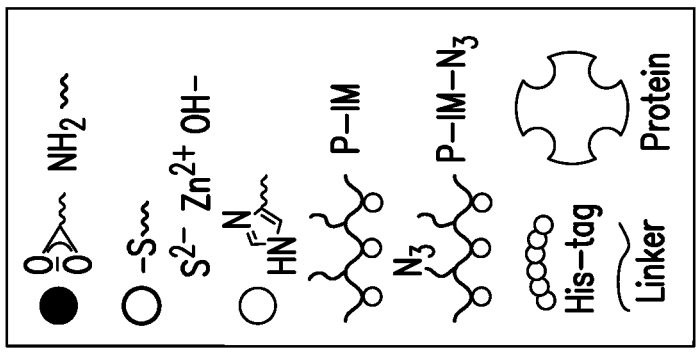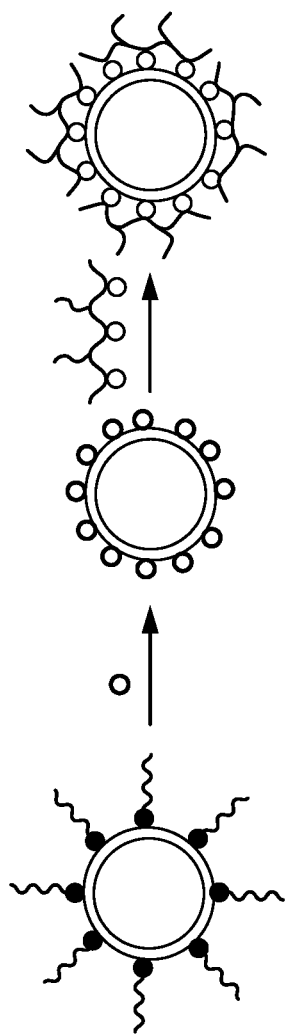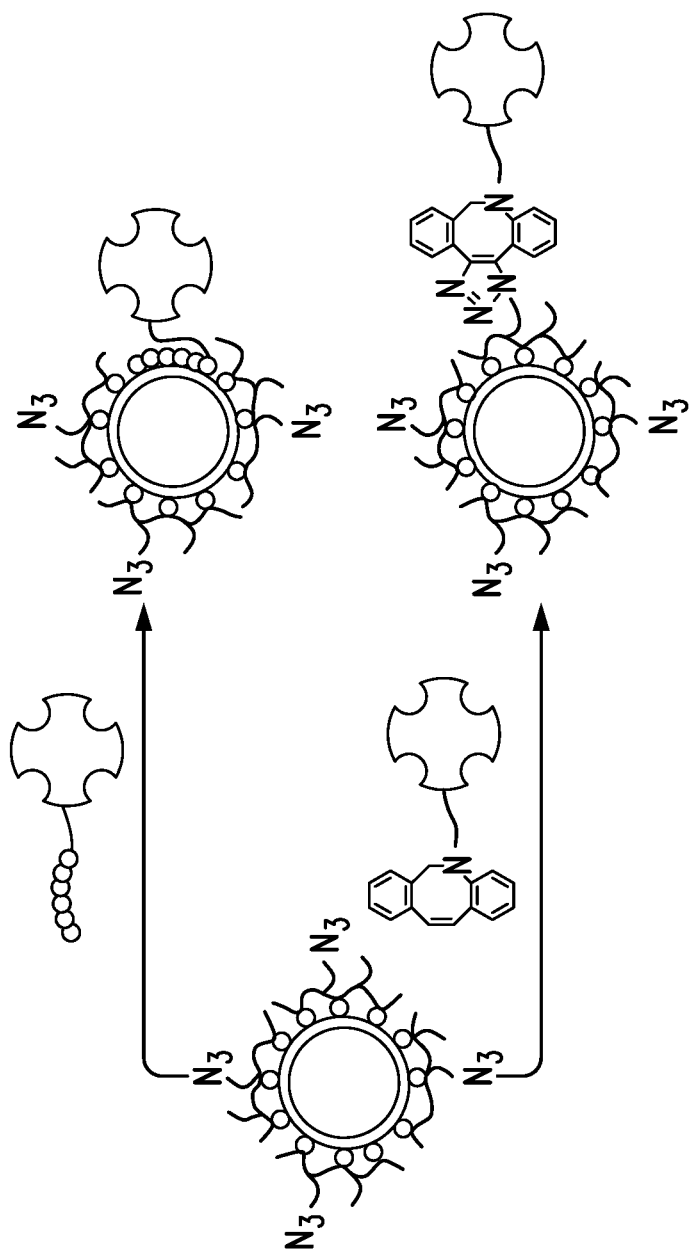
FIG. 2a
FIG. 2b

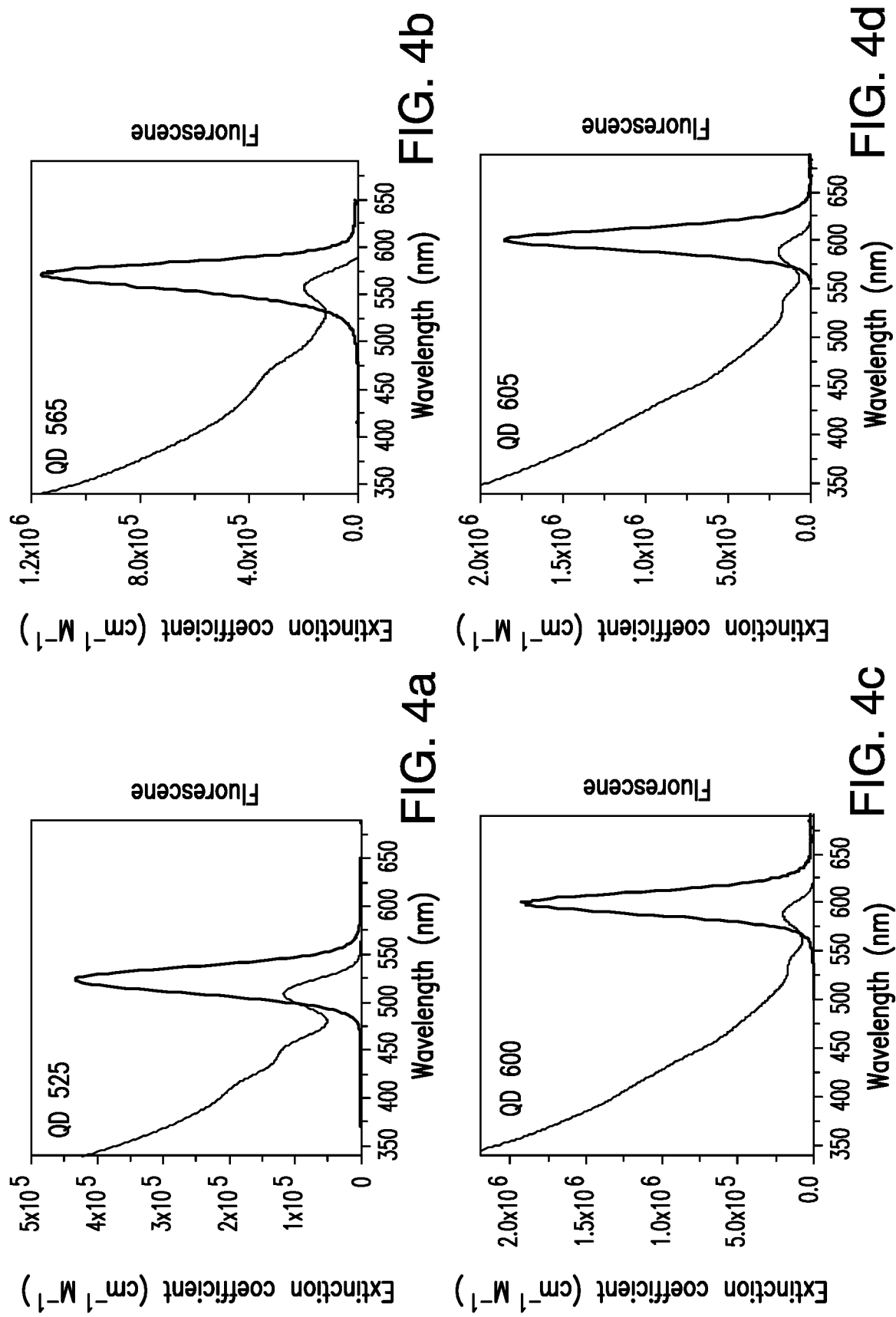

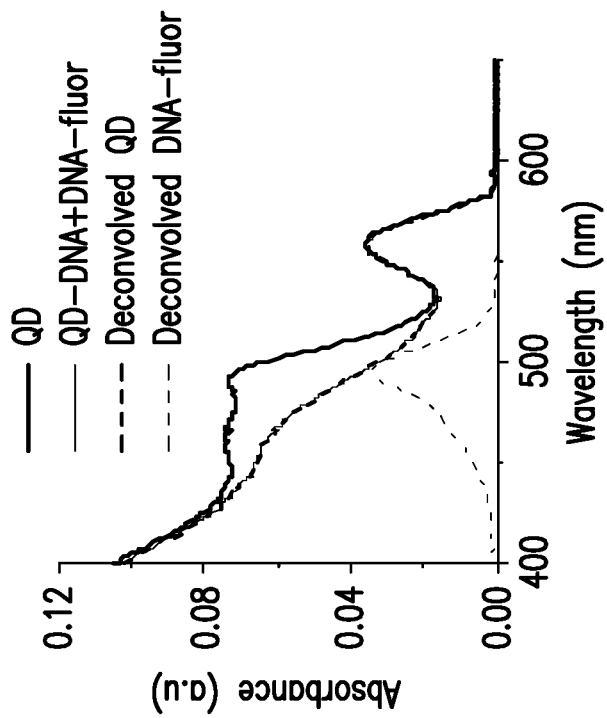
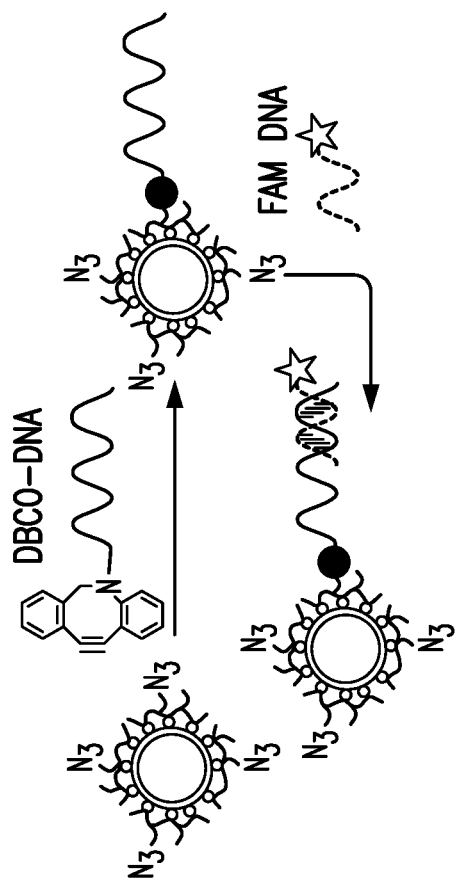
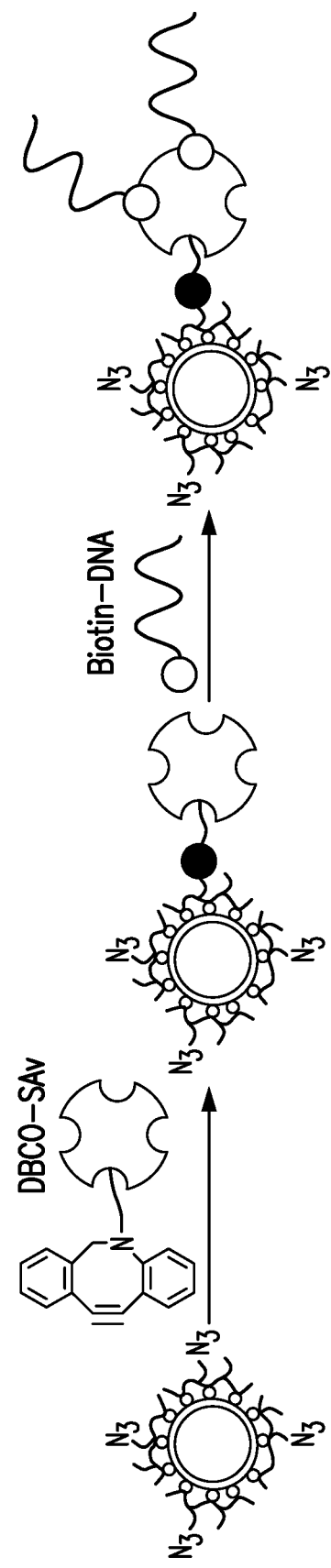
FIG. 7a
FIG. 7b
FIG. 7c

COMPACT AND HOMOGENEOUS QUANTUM DOTS AND METHODS OF MAKING THE SAME

RELATED APPLICATION

This application claims priority to U.S. Provisional Patent Application Ser. No. 62/366,303 filed on Jul. 25, 2016, the disclosure of which is incorporated by reference herein in its entirety.

STATEMENT REGARDING FEDERALLY SPONSORED RESEARCH OR DEVELOPMENT

This invention was made with government support under CA153914 and NS087413 awarded by National Institutes of Health, ES007326 awarded by National Institutes of Health, and 0965918 awarded by National Science Foundation. The government has certain rights in the invention.

BACKGROUND

Quantum dots (QDs) are nanocrystals composed of semiconductors with size-tunable optical and electronic properties. These nanoparticles have been diversely employed as light-absorbing components of solar cells, light-emitting components of LEDs and lasers, and fluorescent probes for biomolecular detection and imaging. Their unique properties primarily arise from the quantum confinement effect, in which excited-state charge carriers (electrons and holes) are confined to sizes smaller than their intrinsic dimensions in the bulk semiconductor material. This results in high efficiency fluorescence emission as well as size-tunable absorption and emission wavelengths. By selecting specific combinations of composition and size, these particles can emit light over an exceptionally broad and continuously tunable spectral range, from the ultraviolet, throughout the visible, and into the near-infrared and mid-infrared. The emission bandwidth is narrow when size distributions are small, and fluorescence quantum efficiencies can approach 100% after epitaxial growth of an insulating shell.

QDs have had a major impact on biomolecular detection and imaging since their first use in cells in 1998. When conjugated to bioaffinity molecules such as antibodies, nucleic acids, and ligands, QDs enable multiplexed detection and monitoring of spectrally distinct molecules and processes using a single excitation source. Their fluorescence emission is typically orders of magnitude brighter and more stable than emission from fluorescent dyes and proteins, allowing continuous monitoring of biological processes for long durations at single-particle sensitivity. This latter feature has enabled the understanding of a multitude of new biological phenomena at the single-molecule level that could not have been readily discerned using conventional techniques and probes.

An ongoing problem in the field of QD-based biomolecular analysis has been the relatively large size of the probes. From commercial suppliers, the hydrodynamic diameter is 15-35 nm, which is much larger than typical globular proteins (~5-10 nm) that QDs are usually used to analyze. Because of this physical disadvantage, the optical advantages of these probes have not yet been fully exploited for many proposed applications. Large QDs cannot access the crowded neuronal synapse, a 20-30 nm space between connected cells, and are largely immobile in the cellular cytoplasm, where macromolecular crowding effects dominate the behavior of colloids. In addition, their large sizes can sometimes impede specific binding to targets and the multivalent nature of conjugation results in unknown stoichiometry to molecular targets.

Minimizing the QD size has proven to be difficult. The hydrodynamic size derives from a combination of contributions from the "hard" crystalline QD and the "soft" coating that is usually organic. A prototypical core/shell CdSe/$Cd_xZn_{1-x}S$ crystalline QD can be very small (3-4 nm), so the coating has been the primary target for focused engineering strategies for size reduction. As-synthesized, QDs are initially coated with aliphatic ligands that render the nanocrystal hydrophobic and insoluble in aqueous solution. Aqueous particles were initially generated using coatings composed of small hydrophilic thiols (e.g. mercaptopropionic acid), silica shells, and amphiphilic polymers and lipids. Monodentate thiols yield very small colloids, but the nanocrystals are only briefly stable in aqueous solution due to oxidation and weak binding strength. However, our groups have recently engineered these coatings for enhanced stability by adding hydrophobic ligand domains to prevent dissociation from the surface. Silica shells allow diverse chemical functionalization, however thin shells have been notoriously challenging to generate reproducibly. Amphiphilic polymers and lipids yield robust particles that are the standard for commercial products, but they necessarily add an additional 5-10 nm of hydrodynamic size that is simply too bulky for many applications.

Recently, multidentate and polymeric ligands have been used to prepare compact nanocrystals that are both highly stable and compact. These coatings are usually based on linear polymers with three types of pendant functional groups that (1) bind to the nanocrystal surface, (2) extend away from the surface to stabilize the particle in aqueous solution, or (3) enable conjugation to a biomolecule. The resulting colloids are stable for months to years and are compatible with harsh purification protocols that destabilize more weakly bound coatings. A variety of polymeric ligands have been reported, synthesized via living radical polymerization, peptide synthesis, or by chemical modification of reactive polymers like polyacrylic acid or poly(maleic anhydride). Surface-binding groups include thiols, imidazoles, and pyridines, and hydrophilic groups include oligo-ethylene glycol (OEG), poly-ethylene glycol (PEG) or zwitterionic betaines, which minimize nonspecific interactions with biological structures such as proteins and cells.

The process of attaching a multidentate polymer to a colloidal surface is not as simple as it is for small molecule ligands. Although the lowest energy conformation of adsorption is through a flat geometry with a maximum number of binding groups associated with the nanocrystal, this conformation can be kinetically difficult to achieve due to competing processes, such as nanocrystal aggregation and polymer crosslinking between particles. The product is often a heterogeneous mixture of small clusters. There is a need for quantum dots and methods of making quantum dots that have a homogeneous dispersion of multidentate polymers on the core. There is also a need for quantum dots that are both compact and homogeneous.

BRIEF DESCRIPTION OF THE DRAWINGS

The features, objects and advantages other than those set forth above will become more readily apparent when consideration is given to the detailed description below. Such detailed description makes reference to the following drawings, wherein:

FIG. 1a. Gel permeation chromatogram of the two samples. FIG. 1b Hydrodynamic size distribution of the two samples measured by single-molecule fluorescence imaging in a mixture of aqueous buffer and glycerol. Detailed synthetic methods are provided in the Examples, below.

FIG. 2a. Schematic illustration of phase transfer and ligand exchange processes through different tested methods. FIG. 2b Schematic illustration of optimized bioconjugation methods using His-tag based self-assembly (upper arrow pathway) and copper-free click chemistry (lower arrow pathway).

FIGS. 4a, 4b, 4c, and 4d. Fluorescence and extinction coefficient spectra: (FIG. 4a) QD525, (FIG. 4b) QD565, (FIG. 4c) QD600, and (FIG. 4d) QD605.

FIG. 5a solvent, FIG. 5b reaction time, FIG. 5c MCR, and FIG. 5d temperature.

FIGS. 7a, 7b, and 7c. Conjugation of QDs to DNA and proteins through click chemistry is efficient and yields bio-functional conjugates. FIG. 7a. Schematic illustration of QD-DNA conjugation reactions through copper-free click chemistry using azide-functional QDs and DBCO-terminated single-stranded DNA (90-mer). Conjugation is validated through hybridization with a complementary DNA terminated with fluorescein (21-mer). FIG. 7b Absorption spectra of QD, QD-DNA hybridized with DNA-fluor, and the deconvolved spectra of the QD and DNA-fluor. FIG. 7c. Schematic illustration of QD-streptavidin (SAv) conjugation reactions through copper-free click chemistry and reactions with biotin-DNA.

FIG. 9a. Quantitative analysis of mobile spots per movie using different samples. Error bar indicates standard error (N=5 for QD-nanobody conjugate; N=3 for control QD) FIG. 9b. Example data of a single QD-nanobody-labeled kinesin position analysis with nanometer accuracy. QD position was measured with 100 ms time resolution and individual traces were fit by a step-finding algorithm. The numbers below the curve are step sizes that the step finding algorithm detected based on the position over time trace. A histogram of step sizes was compiled from 474 steps and 19 traces and fit to a double Gaussian function (center and 2× center), showing a fundamental step size of 8.9 nm, which is in excellent agreement with the predicted 8.3 nm per step for a kinesin labeled at its center of mass position. The 2× center derives from kinesin taking two steps in succession within the 100 ms time resolution.

Figure 1A:
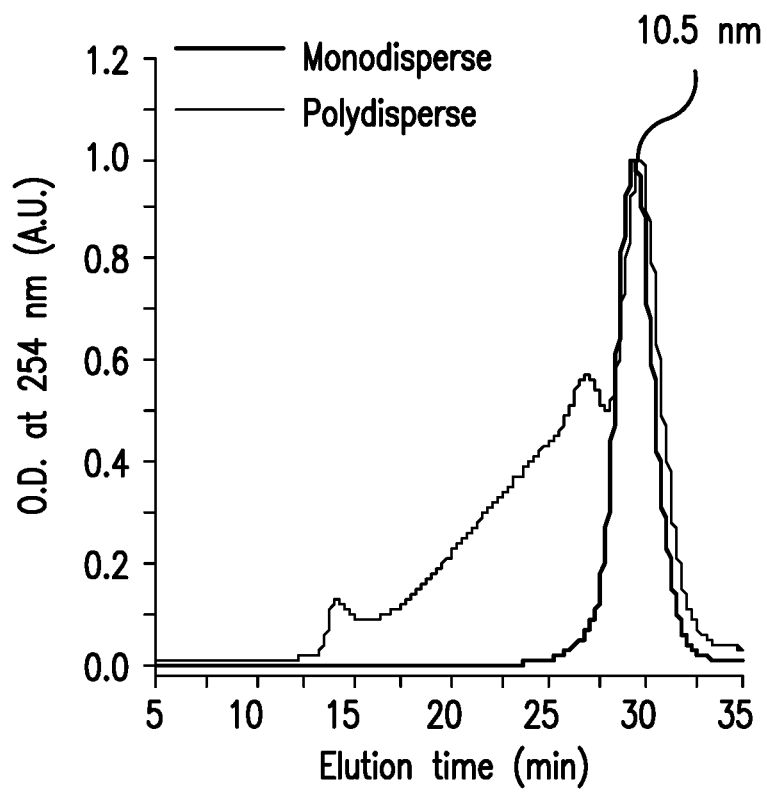
FIGS. 1a and 1b. Comparison of multidentate ligand-coated quantum dot samples that are monodisperse or polydisperse.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments above and the claims below for interpreting the scope of the invention.

DETAILED DESCRIPTION

The compositions and methods now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Likewise, many modifications and other embodiments of the compositions and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

The present disclosure provides new polymeric ligands and optimized coating and bioconjugation methodologies for core/shell (e.g. CdSe/$Cd_xZn_{1-x}S$) quantum dots to generate homogeneous and compact products. The method comprises ligand stripping to rapidly displace nonpolar ligands with weakly binding ligands or ions (e.g. hydroxide ions), allowing homogeneous assembly with polymers (e.g. multidentate polymers) at high temperature. The resulting aqueous quantum dots are about 7-12 nm in hydrodynamic diameter, have quantum yields similar to those in organic solvents, and strongly resist nonspecific interactions due to short oligoethylene glycol surfaces. Compared with a host of other methods, this technique is superior for eliminating small aggregates identified through chromatographic and single-molecule analysis. High-efficiency bioconjugation through azide-alkyne click chemistry and self-assembly with hexa-histidine-tagged proteins that eliminate the need for product purification is also demonstrated. The conjugates retain specificity of the attached biomolecules and are exceptional probes for immunofluorescence and single-molecule dynamic imaging. These results enable broad utilization of compact, biofunctional quantum dots for studying crowded macromolecular environments such as the neuronal synapse and cellular cytoplasm.

Figure 1B:
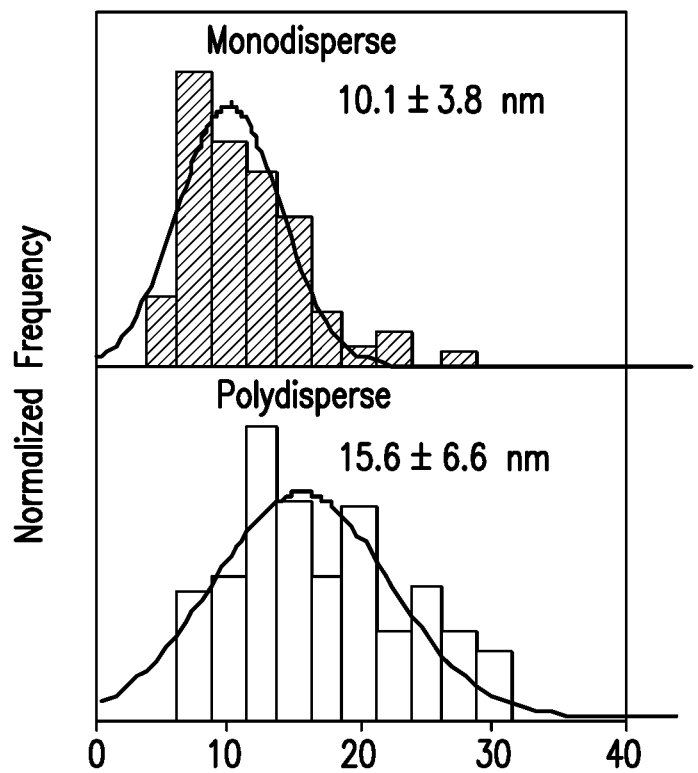

The process of attaching a multidentate polymer to a colloidal surface is not as simple as it is for small molecule ligands. Although the lowest energy conformation of adsorption is through a flat geometry with a maximum number of binding groups associated with the nanocrystal, this conformation can be kinetically difficult to achieve due to competing processes, such as nanocrystal aggregation and polymer crosslinking between particles. The product is often a heterogeneous mixture of small clusters. This outcome is exemplified in FIG. 1, demonstrating that QDs coated with multidentate polymers using slightly different procedures (different polymer amounts and temperature) can yield monodisperse or polydisperse QDs that are virtually indistinguishable by inspection under room light or ultraviolet light, and in terms of stability and quantum yield. But when examined by gel permeation chromatography (GPC, FIG. 1a) or by analyzing their diffusion coefficients at the single molecule level (FIG. 1b), it is clear that one of the samples is highly aggregated while the other is monodisperse. In this disclosure, we characterize products generated through a variety of previously described and novel methods and find that nearly all methods yield some degree of nanoparticle aggregation, but importantly this heterogeneity may not be evident from dynamic light scattering (DLS) or gel electrophoresis measurements which provide insufficient resolution of mixed-size samples (vide infra). For many quantitative imaging and single-molecule analysis applications, achieving a homogeneous, monomeric population is essential, and small populations of clusters skew measurements. To date, ligand exchange processes have not been optimized to maximize monodispersity of QDs coated with multidentate ligands.

In one aspect, a method of making a quantum dot having a substantially homogeneous population of monomeric nanocrystals is provided. The method comprises mixing a nanocrystal coated with weakly binding ligands or ions with polymers in a solution and incubating at temperatures of greater than about 100° C., thereby forming a quantum dot having a substantially homogeneous population of monomeric nanocrystals.

In another aspect, the method comprises incubating for about 1 hour to about 4 hours.

In another aspect, the method comprises coating a core shell nanocrystal that is substantially free of hydrophobic ligands with a plurality of weakly binding ligands or ions, mixing the core shell nanocrystal coated with weakly binding ligands or ions with polymers at a temperature greater than about 100° C., and forming a quantum dot having a substantially homogeneous population of monomeric nanocrystals. The core shell nanocrystals can be made substantially free of hydrophobic residues by ligand displacement from the core shell nanocrystal through the mass-action effect by mixing with a large excess of weakly binding hydrophilic ligands or ions. In one embodiment, the method further comprises conjugating bioaffinity molecules to the quantum dots. In another embodiment, the bioaffinity molecules are conjugated to the quantum dots using copper-free azide-alkyne click chemistry or self-assembly hexa-histidine-tagged proteins techniques, as described herein.

In another aspect, the method comprises making a quantum dot having a substantially homogeneous population of monomeric nanocrystals, the method comprising: removing hydrophobic ligands from a nanocrystal; coating the nanocrystal with a plurality of weakly binding ligands or ions to form a nanocrystal coated with weakly binding ligands or ions; mixing the nanocrystal coated with weakly binding ligands or ions with a polymer in a solution; incubating the mixture, i.e. the resultant solution, at a temperature greater than about 100° C.; and forming a quantum dot having a substantially homogeneous population of monomeric nanocrystals.

In another aspect, the weakly binding ions include, but are not limited to, $Cd^{2+}$, $Zn^{2+}$, $S^{2-}$, $Se^{2-}$, $Te^{2-}$, $OH^-$, $NH_2^-$, $SCN^-$, and $Cl^-$, and combinations thereof.

In another aspect, the weakly binding ion is hydroxide (OH).

In another aspect, the weakly binding ligand is a hydrophilic ligand which include, but are not limited to, mercaptoacetic acid, mercaptopropionic acid, mercaptoundecanoic acid, beta-mercaptoethanol, thioglycerol, mPEG-SH, and OH-PEG-SH, and combinations thereof.

In another aspect, the nanocrystal is selected from $CdSe/Cd_xZn_{1-x}S$, $CdSe/CdS$, $CdSe/ZnS$, $Hg_xCd_{1-x}Se/Cd_yZn_{1-y}S$, or $CdSe_xS_{1-x}/Cd_yZn_{1-y}S$, and combinations thereof, wherein "X" and "Y" in each nanocrystal formula are each independently selected to have a real number value from zero to one, inclusive.

In another aspect the nanocrystal is $CdSe/Cd_xZn_{1-x}S$, wherein "X" can have a value from zero to one, inclusive.

In another aspect the solution is a polar solvent.

In another aspect the polar solvent is selected from dimethyl sulfoxide (DMSO), N-methylformamide (NMF), dimethylformamide (DMF), formamide, acetonitrile, N-methyl-2-pyrrolidone (NMP), ethanol, and methanol, and combinations thereof.

In another aspect the polymer is selected from the group consisting of poly(N-acryloyloxysuccinimide) (PNAS), poly (acrylic acid), poly(maleic anhydride), and their modifications to include thiols, imidazoles, oligoethylene glycols, and azides, and combinations thereof.

In another aspect the polymer is poly(N-acryloyloxysuccinimide) (PNAS).

In another aspect the polymer is treated with an amine containing molecule, an azide, a tertiary amine, a thiol, an imidazole or a monoamine triethylene glycol, and combinations thereof.

In another aspect the polymer is multidentate.

In another aspect the multidentate polymer is selected from P-SH, P-IM and P-IM-N3, and PM-IM.

In another aspect the incubation step occurs at a temperature of about 100° C. to about 130° C.

In another aspect the incubation step occurs at a temperature of about 120° C.

In another aspect the incubation step occurs at a temperature of about 110° C.

In another aspect the incubation step occurs for about 2 hours.

In another aspect the method further comprises conjugating a bioaffinity molecule to the quantum dot.

In another aspect the method further comprises conjugating a bioaffinity molecule to the quantum dot using azide-alkyne click chemistry.

In another aspect the method further comprises coupling the quantum dots with cyclooctynes under ambient conditions in an aqueous solvent to form a cyclooctyne coupled quantum dot; and mixing the cyclooctyne coupled quantum dot with a cyclooctyne modified bioaffinity molecule, thereby attaching the bioaffinity molecule to the quantum dot.

In another aspect the cycloctyne is DBCO.

In another aspect the further comprises conjugating a bioaffinity molecule to the quantum dot using self-assembly hexa-histidine-tagged proteins.

In another aspect the method relates to quantum dots having a substantially homogeneous population of nanocrystals selected from quantum dots having a substantially homogeneous population of amine containing monomeric nanocrystals, and wherein the method further comprises mixing the quantum dots having a substantially homogeneous population of amine containing monomeric nanocrystals with a His-tagged bioaffinity molecule, thereby conjugating the His tagged bioaffinity molecule to the quantum dots.

In another aspect the bioaffinity molecule is selected from nucleic acids, peptides, proteins, antibodies, nanobodies, small molecule ligands, carbohydrates or lipids, and combinations thereof.

In another aspect the present invention relates to a quantum dot made by any of the methods described herein.

In another aspect the present invention relates to a quantum dot comprising a substantially homogeneous population of nanocrystals with a multidentate polymer coating.

In another aspect the quantum dot has a hydrodynamic diameter of about 7 nm to about 12 nm.

In another aspect the present invention relates to a quantum dot, wherein the population of monomeric nanocrystals is greater than about 96% homogenous.

In another aspect the present invention relates to a quantum dot, wherein the population of monomeric nanocrystals is greater than about 99% homogeneous.

In another aspect the present invention relates to a quantum dot wherein the population of multidentate polymers is selected from the group consisting P-SH, P-IM and P-IM-N3, and PM-IM, and combinations thereof.

In another aspect the present invention relates to a quantum dot further comprising a conjugated bioaffinity molecule.

In another aspect the present invention relates to a quantum dot, wherein the bioaffinity molecule is selected from nucleic acids, peptides, proteins, antibodies, nanobodies, carbohydrates and lipids, and combinations thereof.

As used herein, the terms "quantum dot", "dot", "QD" and "nanocrystal" are synonymous and refer to any particle with size dependent properties (e.g., chemical, optical, and electrical properties) along three orthogonal dimensions.

For convenience, the size of quantum dots can be described in terms of a "diameter" or "hydrodynamic diameter." In the case of spherically shaped quantum dots, diameter is used as is commonly understood. For non-spherical quantum dots, the term diameter, unless otherwise defined, refers to a radius of revolution (e.g., a smallest radius of revolution) in which the entire non-spherical quantum dot would fit.

A quantum dot will typically comprise a "core" of one or more first materials and can optionally be surrounded by a "shell" of a second material. A quantum dot core surrounded by a shell is referred to as a "core shell" quantum dot. The term "core" refers to the inner portion of the quantum dot. A core can substantially include a single homogeneous monoatomic or polyatomic material. A core can be crystalline, polycrystalline, or amorphous. A core may be "defect" free or contain a range of defect densities. In this case, "defect" can refer to any crystal stacking error, vacancy, insertion, or impurity entity (e.g., a dopant) placed within the material forming the core. Impurities can be atomic or molecular. The core shell size will depend on the type of materials that make up the core shell.

For example, in a $CdSe/Cd_xZn_{1-x}S$ nanocrystal the core may be composed of Cd and Se, and the outer shell may be composed of Cd, Zn and S, and the amounts of Cd and Se in the core may decrease radially outward, and the amounts of Zn and S may increase (wherein "X" can have a value from zero to one, inclusive, depending on the nanocrystal composition chosen). $CdSe/Cd_xZn_{1-x}S$ nanocrystals are widely used because they can have a small size of about 3-4 nm in diameter while having bright emission in the visible spectrum.

The polymers can include, but are not limited to poly(N-acryloyloxysuccinimide (PNAS), poly(acrylic acid), poly (maleic anhydride), and their modifications to include thiols, imidazoles, oligoethylene glycols, and azides. In some embodiments, the polymers are multidentate. As used herein, the term "multidentate polymer" or "polymer multidentate ligand" means a polymer or copolymer containing 2 or more repeat units that are suitable ligands for binding to nanoparticles such that the polymer acts as a multidentate ligand in its binding to the nanoparticle surface. It will be understood that if the polymer is too long, it will cause the nanoparticles to precipitate (i.e., it will act as a flocculent). Therefore, the polymer multidentate ligand preferably has at most from about 2 to about 2500 repeat units, more preferably from 5 to 1000, and most preferably from 10 to 250.

Conventional polymers can be thought of as multidentate ligands if a suitable functionality can be introduced as a part of the pendant group in the repeat unit. The polymers can be reacted with compounds containing primary amines that conjugate to the polymer backbone through an amide bond. For example, any of the polymers listed above can contain, or be treated to contain, a thiol (cysteamine) (SH), an imidazole (histamine) (IM) a monoamine triethylene glycol (NH2-EG3-OH) (IM-N3), or a tertiary amine, and the like. For example, in some embodiments, the multidentate polymer is PNAS having a thiol (P-SH), PNAS having an imidazole (P-IM), and PNAS having monoamine triethylene glycol (P-IM-N3). Any other modifications of the polymers which allow for the formation of multidentate polymers can be used. In one embodiment, the polymer is a polymer reacted with a compound containing a primary amine.

In one embodiment, the molar capping ratio of the polymer is about 1:1 to about 1:5. In an exemplary embodiment, the molar capping ratio of the polymer is about 1:5. By molar capping ratio (MCR), it is meant the ratio of the number of imidazole or thiol groups (which bind to the quantum dot surface), per the total number of quantum dot surface atoms.

An important step of the method for making quantum dots having a substantially homogeneous population of monomeric nanocrystals, is mixing the nanocrystals having weakly binding ligands or ions with polymers or multidentate polymers in a solution and incubating at a temperature greater than about 100° C. In one embodiment the temperature is about 100° C. to about 130° C., preferably 120° C. In another embodiment, the temperature is about 110° C. The incubation step occurs between about 1 hr to about 4 hr. In one embodiment, the incubation step occurs for about 2 hours.

In another aspect, the present disclosure also provides quantum dots comprising a substantially homogeneous population of monomeric polymers or multidentate polymers on a nanocrystal.

In another aspect, quantum dots made by the process of any of the methods described herein are provided.

The quantum dots of the present disclosure comprise a substantially homogeneous population of monomeric nanocrystals. The term "substantially homogenous population of monomeric nanocrystals" refers to a population of nanoparticles having substantially identical size and shape. One of ordinary skill in the art will realize that particular sizes of nanocrystals are actually obtained as particle size distributions. For the purpose of the present disclosure, a substantially homogenous population of monomeric nanocrystals means that at least about 80% of the particles or, in some cases, about 80% to about 99%, about 96%, about 99%, or about 100% of the monomeric nanocrystals, fall within a specific particle size range, and the particles deviate in diameter or largest dimension by less than 20% rms (root-mean-square) deviation and, in some cases, less than 10% rms deviation, and, in some cases, less than 5% rms deviation. In a particular embodiment, the quantum dots comprise a population of monomeric nanocrystals that are greater than about 96% homogeneous. In another embodiment, the quantum dots comprise a population of monomeric nanocrystals that are greater than about 99% homogeneous.

Generally, quantum dots of the present invention can have an average hydrodynamic diameter of about 7 nm to about 12 nm. It should be noted that the size of the quantum dot can vary depending on the type of nanocrystal used, and different types of nanocrystals can have different hydrodynamic diameters. It is possible that an undiscovered type of nanocrystal, having even smaller diameters, could be used in this method to produce quantum dots smaller than 7 nm. The methods described herein and the resulting quantum dots allow for a substantially homogeneous monodispersed population of polymers, allowing for the creation of quantum dots at a size of about less than 12 nm, and which range from about 7 nm to about 12 nm.

In a further embodiment, the quantum dots of the present disclosure, made from the methods described above, can be conjugated to bioaffinity molecules. As used herein, the term "bioaffinity molecule" and its variants comprises any compound, as well as analogs (including engineered and/or synthetic analogs), derivatives, mutants or variants and/or biologically active fragments of compounds that can bind a biomolecule. In one embodiment, the bioaffinity molecule is selected from a protein, peptide, nucleic acid, nucleotide, antibody, nanobody, carbohydrate or lipid, as well as combinations of the foregoing. As used herein, the term "biomolecule" and its variants comprises any compound isolated from or residing within or external to a living organism, as well as analogs (including engineered and/or synthetic analogs), derivatives, mutants or variants and/or biologically active fragments of the same. For example, the biomolecule can be a protein (e.g., an enzyme), peptide, nucleic acid, nucleotide, carbohydrate or lipid, including those present intracellularly, or present on cell surfaces, cellular structures, particular tissue or organs, particular microbials, and the like. The quantum dots described herein, when conjugated to bioaffinity molecules, can be used to detect and identify biomolecules, which can be used to detect and identify cell and tissue types, cellular structures, microbials, microbial structures, proteins, peptides, antigens, nucleic acids, and the like. Bioaffinity molecules can have their own fluorescence or be attached to a molecule having fluorescence, allowing for the detection of biomolecules in vivo, in vitro, and in situ.

In certain embodiments, the fluorescent molecules are conjugated to a biological molecule or targeting molecule which can be a nucleic acid, polypeptide, cell, antibody, epitope, protein, inhibitor, receptor, receptor substrate, small molecule ligands, to render them specific to biological targets, see, for example, Smith et al., Adv. Drug Deliv. Rev. 60, 1226-1240 (2008).

This conjugation can be accomplished using standard bioconjugation protocols, such as the coupling of maleimide-activated QDs to the thiols of reduced antibodies. QDs disclosed herein may emit fluorescence without an external source of excitation when conjugated to enzymes that catalyze bioluminescent reactions, due to bioluminescence resonance energy transfer (BRET). See So et al., Nat. Biotechnol. 24 (2006), pp. 339-343, hereby incorporated by reference.

In certain embodiments, quantum dots disclosed herein can be cross-linked to small molecule ligands, inhibitors, peptides, proteins, antibodies, nanobodies, carbohydrates, lipids, and nucleic acids which can bind with high specificity to many different cellular receptors and targets.

In a particular embodiment, the quantum dots disclosed herein are conjugated to bioaffinity molecules using copper-free azide-alkyne click chemistry and self-assembly hexa-histidine-tagged proteins technique described herein.

The quantum dots can be conjugated to the bioaffinity molecule using novel adaptor molecules for copper-free azide-alkyne click chemistry comprising making the quantum dot to have a amine containing polymer with about 20% of the OEG groups terminated in azides, and coupling this polymer to a cycloooctynes (e.g. dibenzylcyclooctyne-DBCO) under ambient conditions in aqueous solvents, after attachment of the cyclooctynes to a bioaffinity molecule, thus conjugating the bioaffinity molecule to quantum dot, as shown in FIG. 2b.

The quantum dots can also be conjugated to a bioaffinity molecule mixing the quantum dot with His tagged bioaffinity molecules, thereby conjugating the bioaffinity molecule to the quantum dot, as shown in FIG. 2b.

EXAMPLES

The following examples further describe and demonstrate embodiments within the scope of the present invention. The Examples are given solely for purpose of illustration and are not to be construed as limitations of the present invention, as many variations thereof are possible without departing from the spirit and scope of the invention.

Example 1 Method of Making Quantum Dots

As depicted in FIGS. 2a and 2b, a new methodology for homogeneous and compact polymeric assembly on a QD surface using a two-step process was optimized, whereby the initial hydrophobic ligands are removed from the nanocrystal surface and replaced with weakly bound ligands or ions. We found that a rapid process using hydroxide ions renders the nanocrystals homogeneously dispersible in polar solvents, in which multidentate polymers can readily displace the weakly bound ions without destabilizing the dispersion. A critical step is to heat the QD-polymer mixture at high temperature (>about 100° C.) to dissociate small clusters and boost quantum yield, generating homogeneously coated nanocrystals that are exceptionally stable in aqueous solution. This new process is shown to substantially improve the quality of the products and is much more rapid than previous multi-step coating techniques. Using these new methods, we demonstrate the generation of small, stable, and multicolor QDs in the range of 7.4-11.6 nm with negligible nonspecific association with cells.

It is further demonstrated that these nanocrystals can be functionalized with biological molecules using copper-free azide-alkyne click chemistry and self-assembly with molecules containing a His-tag. Unlike frequently used amide-generating bioconjugation reactions (e.g., EDC/NHS chemistry), the reaction yields for these methods are very high, prevent protein cross-linking, and do not require extensive purification. It has been demonstrated that the QDs can be used for a broad range of biomolecular detection and imaging applications, as DNA conjugates retain their molecular affinity toward hybridization with complementary DNA sequences, antibody conjugates specifically stain cellular antigens, and conjugates to small antibody fragments specifically bind to tagged motor proteins to allow precise measurements of single-molecule motion. These results will enable the broad adoption of multidentate polymer ligands for quantum dot coating and enhance the utility of QDs for applications requiring highly compact, monodisperse, and stable single-molecule probes.

Design and Synthesis of Multidentate Ligands.

Figure 3:
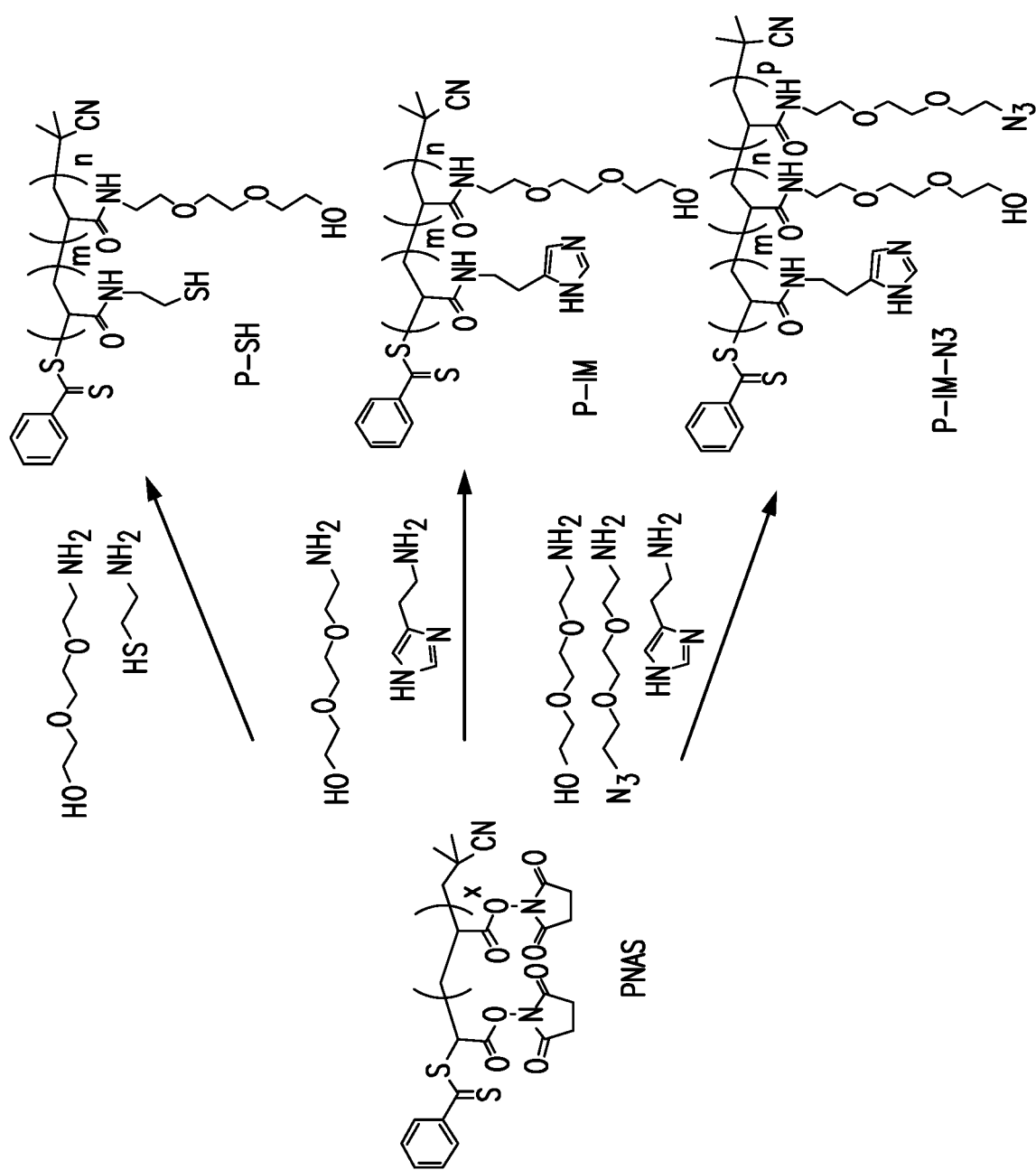
FIG. 3. Synthesis of multidentate ligands through modification of poly(N-acryloyloxysuccinimide (PNAS).

Multidentate polymer ligands were designed to allow modular control of chemical structure, a variety of binding groups, and a high graft density of OEG to minimize nonspecific interactions with biological molecules and cells. Polymers were synthesized starting from a linear homopolymer of amine-reactive N-hydroxysuccinimide (NHS) functional groups, poly(N-acryloyloxysuccinimide) (PNAS). PNAS was synthesized via reversible addition fragmentation chain transfer (RAFT) polymerization to yield a polymer with 18,900 Da molecular weight, or approximately 110 NHS groups, with a polydispersity index of 1.2 (assessed through GPC). As depicted in FIG. 3, PNAS was reacted with compounds containing primary amines that conjugate to the polymer backbone through an amide bond. The compounds contained either a thiol (cysteamine) or imidazole (histamine) to bind to QD surfaces, or a monoamine triethylene glycol (NH2-EG3-OH) to render stability in aqueous solution and minimal nonspecific interactions with cells and biological molecules, and minimal size. The molar feeding ratio of the binding group compound to the hydrophilic group was, and separate polymers were created containing thiols (P-SH) or imidazoles (P-IM) in order to compare how the binding group impacts coating. A third polymer (P-IM-N3) was prepared to contain reactive azide groups using a monoamine, monoazide triethylene glycol (NH2-EG3-N3) that replaced 20% of NH2-EG3-OH in P-IM.

Quantum Dot Nanocrystals.

Quantum dots composed of CdSe cores capped with $Cd_xZn_{1-x}S$ shells were synthesized using typical high temperature organic-phase arrested precipitation and layer-by-layer shell growth methods. Shells were grown in 0.8 monolayer (ML) increments in order to suppress shell material nucleation and were graded in composition from higher CdS content on the CdSe surface to outer layers that were entirely ZnS to aid in stability of the final particle. By tuning both the core size and the shell thickness, the nanocrystals could emit light in the range of 520-610 nm with a fluorescence quantum yield (QY) greater than 40% in hexane or chloroform after purification. For this work, we prepared four batches with different nanocrystal sizes with emission wavelengths indicated by their names: QD525 with 3.3±0.3 nm diameter, QD565 with 4.3±0.5 nm diameter, QD600 with 5.7±0.5 nm diameter, and QD605 with 5.5±0.5 nm diameter; sizes were determined by transmission electron microscopy (TEM)). After synthesis the nanocrystals were coated with aliphatic ligands such as oleylamine and oleic acid, the predominant ligands in the shell growth solution.

Multidentate Ligand Coating Methods.

It was empirically found that the attachment of polymeric ligands to QD surfaces is challenging to control and is more difficult for nanoparticles with larger sizes, likely due to lower surface energy compared with smaller particles that allows competing aggregation processes to dominate. In this work, we focused on maximizing the homogeneity of QD605 coated with P-IM and P-SH by tuning the coating conditions. For homogeneous coating, it is critical to judiciously select QD coatings, solvents, and physical conditions that stabilize the surface of the nanocrystal as well as the polymer to prevent aggregation. The ligands on the surface during exchange and the temperature were found to be important parameters. First, ligands on the nanocrystal surface were tuned and mixed with the multidentate polymeric ligands P-IM or P-SH in solvents optimized to stabilize both the QDs with their initial ligands and the polymer-coated QDs. For each sample, the final transfer efficiency was measured to aqueous solution, the fluorescence quantum yield, the hydrodynamic size using dynamic light scattering (DLS) and gel permeation chromatography (GPC) calibrated with molecular weight protein standards with known diameters, and the homogeneity of migration through an agarose-polyacrylamide gel via electrophoresis. The six intermediate ligands and methods (M1-6) are summarized in Table 1 and included native hydrophobic ligands in $CHCl_3$ (M1), hydrophilic monodentate ligands that are short-chain (thioglycerol, M4) or long-chain (PEG-SH, M5), or three ligand-free approaches. The ligand-free coatings were developed by Talapin and coworkers to "strip" the native hydrophobic ligands from the surface, yielding nanocrystals surfaces terminated with sulfide ions (M2), zinc ions (M3) or hydroxide ions (M6).

TABLE 1

Characterization of QD605 coated with multidentate ligands prepared via six different phase transfer methods.

| Method | Ligand | Polymer | Transfer Efficiency (%) | Quantum Yield (%) | Size by $DLS^a$ (nm) | Size by $GPC^b$ (nm) |
|---|---|---|---|---|---|---|
| M1 | Hydrophobic ligands | P-IM | 28.3 | 21.7 | 30.8 ± 11.8 | >30$^c$ |
| | | P-SH | 31.2 | 39.0 | 25.5 ± 7.9 | 17.5 |
| M2 | $S^{2-}$ | P-IM | 47.0 | 18.5 | 14.9 ± 3.3 | >30 |
| | | P-SH | 32.4 | 9.0 | 12.7 ± 2.3 | 16.3 |
| M3 | $Zn^{2+}$ | P-IM | 38.6 | 32.6 | 53.9 ± 16.4 | 17.1 |
| | | P-SH | 41.1 | 33.2 | 18.0 ± 7.6 | 16.5 |
| M4 | Thioglycerol | P-IM | 65.4 | 35.8 | 19.2 ± 5.6 | 15.2 |
| | | P-SH | 59.1 | 31.7 | 17.3 ± 4.6 | 16.5 |

TABLE 1-continued

Characterization of QD605 coated with multidentate ligands
prepared via six different phase transfer methods.

| Method | Ligand  | Polymer | Transfer Efficiency (%) | Quantum Yield (%) | Size by DLS[a] (nm) | Size by GPC[b] (nm) |
|--------|---------|---------|-------------------------|-------------------|---------------------|---------------------|
| M5     | mPEG-SH | P-IM    | 48.5                    | 29.0              | 14.6 ± 3.3          | 14.2                |
|        |         | P-SH    | 55.8                    | 22.3              | 15.0 ± 3.8          | 14.6                |
| M6     | OH⁻     | P-IM    | 66.5                    | 17.8              | 10.2 ± 2.6          | 12.5                |
|        |         | P-SH    | 70.4                    | 16.1              | 14.0 ± 2.8          | N.A.[d]             |

[a]Hydrodynamic size measured by DLS is the mean size from the number distribution.
[b]The size measured by GPC is the minimum size among peaks, calculated from calibration curves of proteins with known size.
[c]Sizes above 30 nm exceed the GPC column limit.
[d]No signal detected.

The results are summarized in Table 1. Importantly, all coatings yield stable colloidal dispersions of QDs in aqueous solution with substantial QY. The products were lowest in quality for methods in which the intermediate coatings were hydrophobic ligands, sulfides, and zinc ions (methods M1-M3), which had low transfer efficiencies (<50%), large sizes (>16 nm by GPC), and smeared gel bands. The products were particularly aggregated using the P-IM polymer with hydrophobic and sulfide coatings and could not migrate into the gel during electrophoresis. Importantly for these clustered samples there was little correlation between average size by DLS and the major population of products observed via GPC. In addition, the degree of band "smearing" showed little correlation with GPC analysis, as many of the gel bands appeared to be highly uniform (e.g. M5 P-SH), but all samples tested contained a significant population of clusters revealed by GPC. Smaller sizes and improved transfer efficiencies were obtained with the two thiol ligands and the hydroxide surface coating (methods M4-M6). The results were particularly improved with the hydroxide surface (M6), which yielded the smallest sizes by DLS and GPC and the highest transfer efficiency (>65%). This reagent was also lowest in cost, and the procedure was much more rapid compared with the ones requiring an intermediate thiol. However this method was only effective with the P-IM polymer, as the thiol-based P-SH polymer yielded products that could not elute through the GPC column, likely due to oxidative disulfide formation in the alkaline coating solution that can cross-link particles. We therefore elected to proceed with further optimization using the imidazole-based polymer and method M6.

Optimization of Polymer Coating Via Ligand Stripping.

Figure 5A:
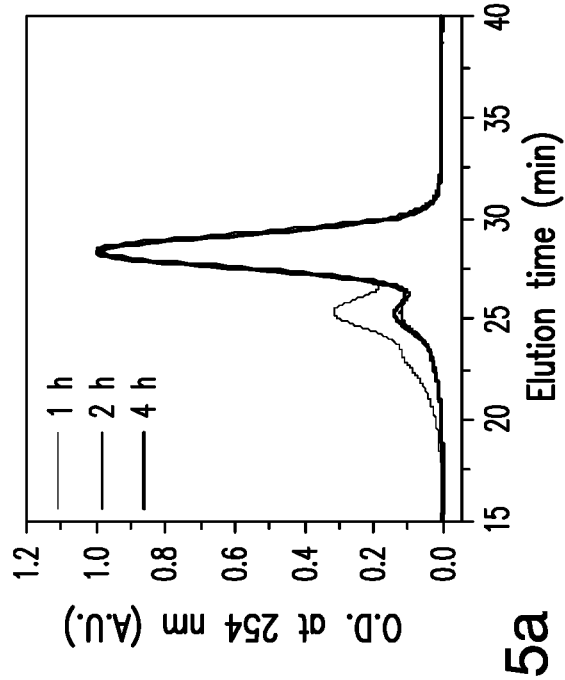
FIGS. 5a, 5b, 5c, and 5d. Optimization of coating methods for hydroxide-capped QD605 QDs with P-IM by changing solvents (DMSO, NMF, methanol), reaction time (1 h, 2 h, 4 h), molar capping ratio (MCR; 1:1, 2:1, 5:1) and temperature (room temperature, 70° C., 110° C.). Gel permeation chromatograms of aqueous products using different coating conditions, adjusting.
Figure 5B:
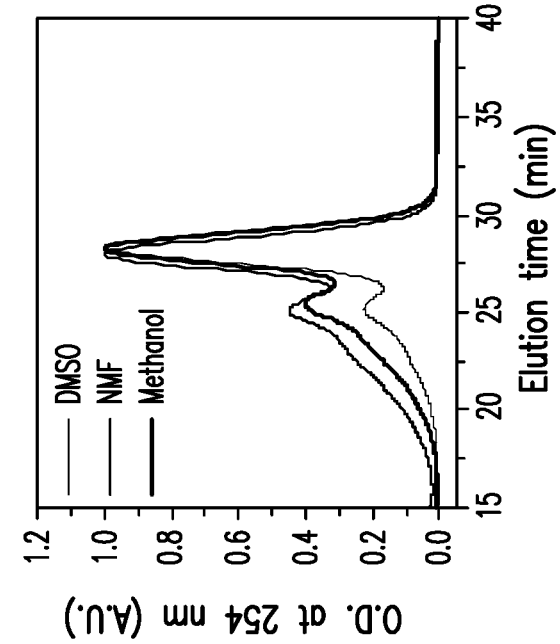
Figure 5C:
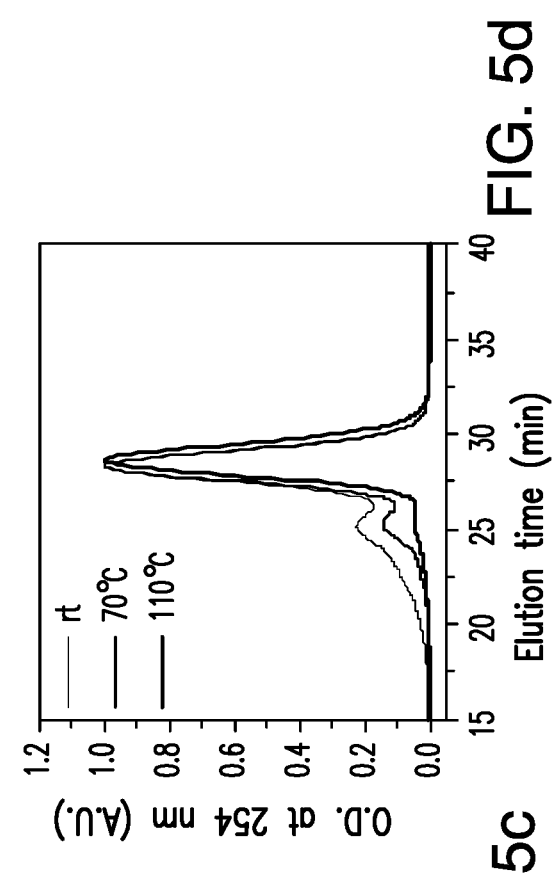
Figure 5D:
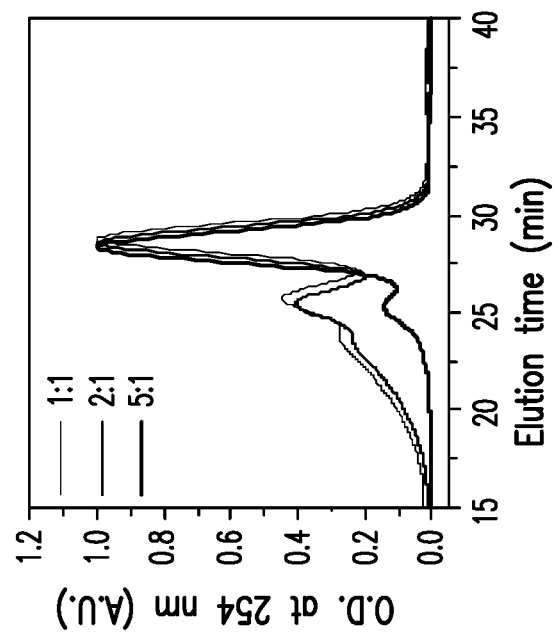

Hydroxide-coated QDs effectively have bare, ligand-free surfaces, with a zeta potential near −26 mV, which provides strong electrostatic repulsion for stabilization in polar solvents such as N-methylformamide (NMF) and dimethylsulfoxide (DMSO). These surfaces provide an ideal substrate for adsorption of polymeric ligands because the particles are highly resistant to aggregation, the inorganic hydroxide adsorbates are readily displaced, and the polar solvent readily dissolves all of the reagents. However, when the coating procedure was performed at room temperature, GPC revealed that despite a small size observed by DLS (10.2 nm), a large fraction of the population was present as small aggregates when using the P-IM polymer. As shown in FIG. 5, the hydroxide-mediated polymeric coating strategy was further optimized by adjusting specific reaction parameters (solvent, reaction time, molar capping ratio, and temperature), with outcomes summarized in Table 2. All particles were stable in aqueous solution after purification and yielded fluorescent, transparent dispersions. The major characteristics for optimization were GPC size and homogeneity, shown in FIGS. 5a, 5b, 5c, and 5d. The major peak with smallest size was deemed to be the unaggregated monomeric QD population, and we quantified its fraction in the population by fitting the chromatograms to a sum of Gaussian peaks, dividing the area of the monomeric QD peak by the total area under the GPC curve. With hydroxide methods, DMSO was the best of three solvents tested for minimizing aggregate peaks (FIG. 5a), and a 2 h reaction time was found to be optimal, with no benefit provided by longer times (FIG. 5b). Adding excess polymer was found to be beneficial based the result of varying the molar capping ratio (MCR) which was calculated as the ratio of the number of imidazole groups on the polymer per the total number of QD surface atoms (FIG. 5c). To fully minimize the aggregate population, it was most important to use high temperatures for coating (about 110° C.), which removed small aggregates present, likely due to dissociation of weakly bound conformations of the polymer that were not fully adsorbed (FIG. 5d). With high temperatures in DMSO and with excess polymers, the monomeric QDs were present at >96% of the entire population, with a diameter of 10.4 nm by DLS and 11.6 nm by GPC. Sequential optimization of each parameter was critical for minimizing the fraction of aggregate population, and further tweaking of these optimized parameters resulted in nearly 100% monomeric QDs by GPC.

TABLE 2

Characteristics of P-IM-coated QD605 with different coating conditions

| Reaction parameter       |         | QY (%) | Size by DLS (D, nm) | Size by GPC (D, nm) | Monomeric QDs (%) |
|--------------------------|---------|--------|---------------------|---------------------|-------------------|
| Solvent[a]               | DMSO    | 20.8   | 11.6 ± 2.6          | 11.9                | 64.0              |
|                          | NMF     | 17.8   | 13.5 ± 3.3          | 12.1                | 42.0              |
|                          | Methanol| 13.9   | 11.4 ± 2.5          | 11.9                | 45.8              |
| Time[b]                  | 1 h     | 36.4   | 12.1 ± 2.7          | 11.9                | 69.9              |
|                          | 2 h     | 46.9   | 12.2 ± 2.4          | 11.9                | 92.1              |
|                          | 4 h     | 34.5   | 11.0 ± 3.3          | 11.9                | 87.9              |
| Polymer Amount (MCR)[c]  | 1:1     | 20.3   | 11.0 ± 2.9          | 11.7                | 39.9              |
|                          | 2:1     | 25.2   | 13.1 ± 1.9          | 11.8                | 50.0              |
|                          | 5:1     | 46.9   | 12.2 ± 2.4          | 11.9                | 92.1              |
| Temperature[d]           | r.t     | 20.8   | 11.6 ± 2.6          | 11.9                | 77.4              |
|                          | 70° C.  | 34.5   | 11.0 ± 3.3          | 11.9                | 92.1              |
|                          | 110° C. | 47.4   | 10.4 ± 2.4          | 11.6                | 95.7              |

[a]Solvent tuned with fixed reaction time (5 h), MCR (5:1), and temperature (70° C.).
[b]Time tuned with fixed solvent (DMSO), MCR (5:1), and temperature (70° C.).
[c]MCR tuned with fixed solvent (DMSO), reaction time (2 h), and temperature (70° C.).
[d]Temperature tuned with solvent (DMSO), reaction time (2 h), and MCR (5:1). r.t. = room temperature.

Figure 6:
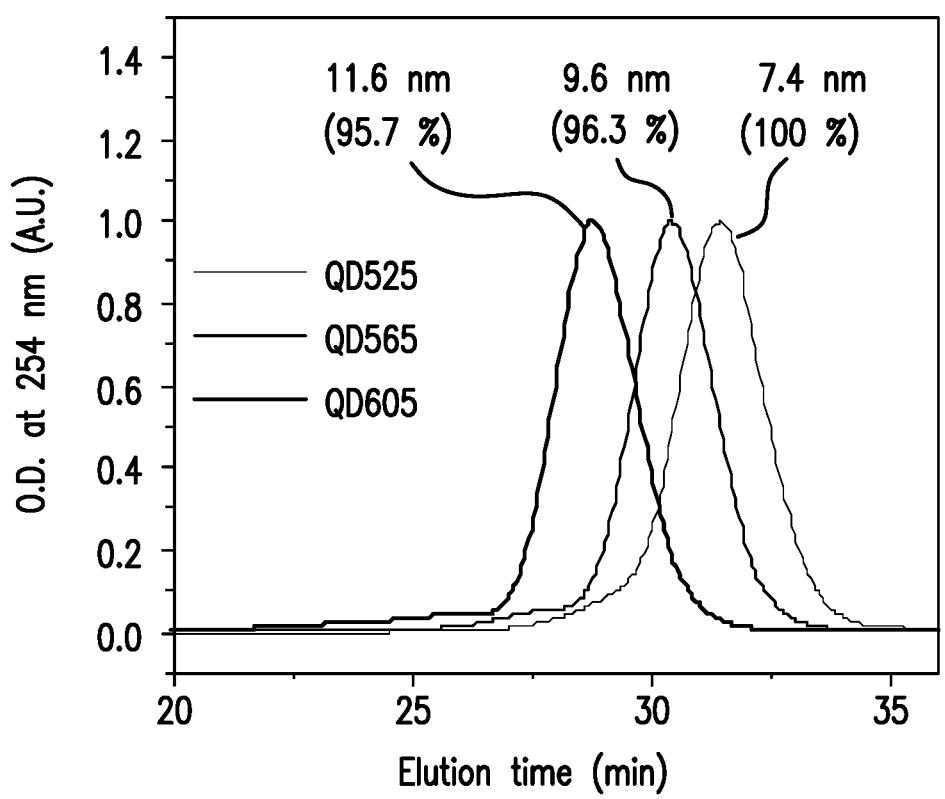
FIG. 6. Extension of the optimized coating method for preparation of P-IM-coated QDs with different sizes and colors. Their corresponding gel permeation chromatograms are shown.

Trends in QY in aqueous solution mirrored trends in aggregation: the monomeric percentage correlating with QY with an $R^2$ of 0.71, indicating that the aggregates likely have lower QY. The QY for QD605 using the optimized method was 47.4%, which is similar to that measured in organic solvent. Reduced QY in aqueous solution for quantum dots coated with multidentate polymer ligands results in part from small aggregates that are not readily observed with measurement techniques like DLS. Thus optimization coupled with high resolution characterization can improve the final optical properties. Using this new methodology, three sizes of QD cores were coated, which yielded high-QY particles that were stable in aqueous solution with small sizes (7.4-11.6 nm) by GPC. These hydrodynamic sizes were just 4-6 nm larger than their hard-core TEM sizes. Based on the expectation of ~5 nm increase in hydrodynamic size by measuring the molecular length of the polymer from the imidazole group to the end of an adjacent OEG, this compact QD is consistent with a flat conformation of polymeric coating on the nanocrystal surface. Their narrow size distributions by GPC (FIG. 6) indicate homogeneity of the monomeric product, comprising 96-100% of the total distribution. The zeta potential for QD605 at pH 7.4 was −11.0±1.2 mV, consistent with previous reports of nanocrystals coated with OEG, and the particles were stable for months without detectable change in properties, even with harsh purification procedures.

Example 2—Conjugation to Nucleic Acids and Proteins and Functionality Assays

Figure 8:
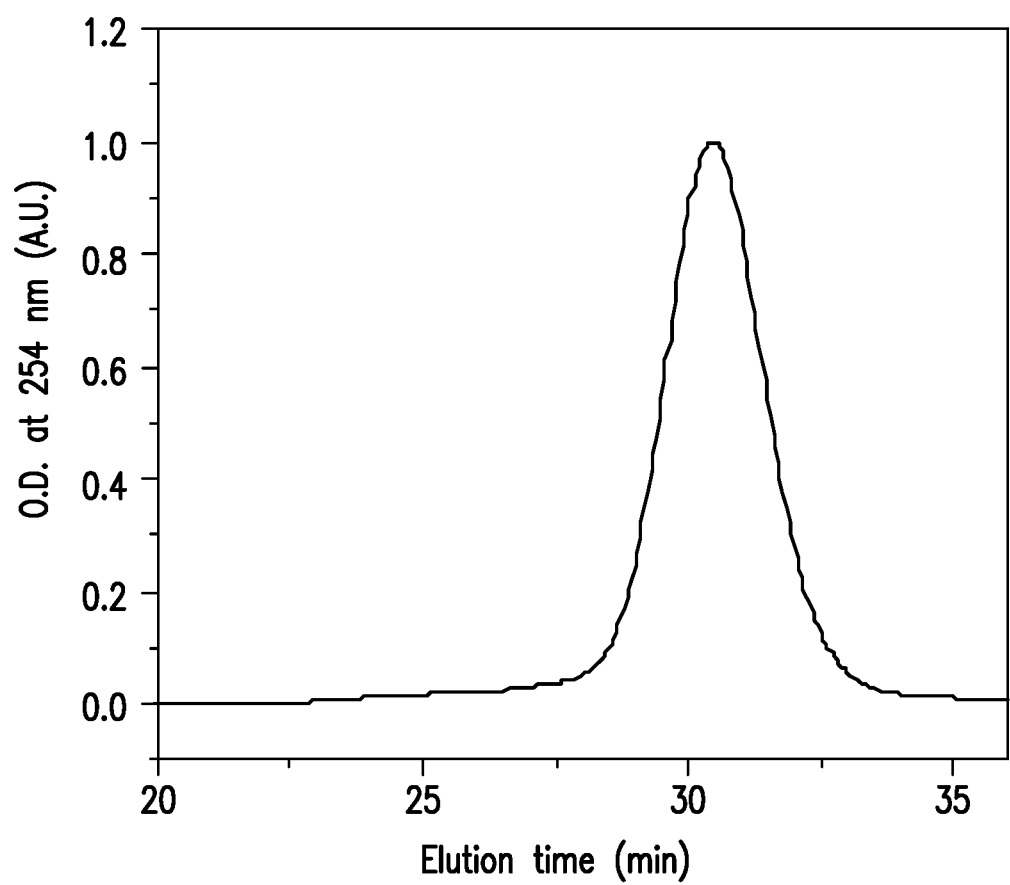
FIG. 8. Gel permeation chromatogram of QD565 coated with P-IM-$N_3$ polymer.

Compact QDs are similar in hydrodynamic size to many of the biological molecules to which they are conjugated, such as globular proteins. Because simple purification methodologies are usually based on size, it is critical that conjugation reactions go essentially to completion because purification from unreacted biomolecules may not be efficient. Two high-efficiency methodologies were developed for our optimized compact particles, using His-tag-based self-assembly and azide-alkyne click chemistry. For click chemistry, we prepared a variant of the P-IM polymer for which 20% of the OEG groups were terminated with azides, which can be coupled to strained cyclooctynes such as dibenzylcyclooctyne (DBCO) under ambient conditions without catalysts in aqueous solvents (FIG. 7a). QDs coated with this polymer had a similar size and homogeneity as those coated with P-IM (see FIG. 8), and upon mixing with biological molecules modified with DBCO, reactions were found to be highly efficient based on mobility shifts in agarose-acrylamide gel electrophoresis. DNA oligomers terminated with DBCO mixed with QDs increased the migration distance of QD, consistent with an increase in charge. Discrete bands were observed indicative of specific bioconjugate valencies, and after 48 h reaction under ambient conditions, a 1:1 DNA:QD mixture was 64.5% complete, measured by depletion of the unconjugated QD band. The biofunctionality of the attached DNA was verified by mixing these QD-DNA conjugates with a complementary DNA sequence end-labelled with a fluorophore (fluorescein; DNA-fluor), which bound to the DNA-conjugated QD but not the QD alone, indicated by their absorption spectra after purification and the deconvolved contributions from the absorbing components (FIG. 7b).

Azide-functional QDs were also conjugated with streptavidin (SAv) modified with DBCO using NHS-DBCO (see FIG. 7c). DBCO-SAv specifically conjugated to the QDs based on gel electrophoresis shifts and a 24 h reaction with SAv:QD molar ratio ≥1 was found to be efficient based on the disappearance of the unconjugated QD gel band. SAv-QD conjugates retained functional binding to biotin, as assessed by mixing with biotin-terminated DNA which yielded a gel shift relative to SAv-QDs. The two gel bands that appear at higher biotin-DNA:QD ratios (>1.6) may derive from QDs bound to 1 or 2 SAv proteins within the distribution, however additional analysis is needed to validate this. Nevertheless, it can be deduced that biotin conjugation to SAv-QDs is efficient based on depletion of the SAv-QD band and the absence of additional gel shifts for biotin-DNA reactions with a DNA:QD ratio higher than 4:1 (SAv is a tetramer capable of binding up to 4 biotins but likely cannot be fully saturated in this experiment due to steric and/or electrostatic repulsion). These findings of high reaction efficiencies are important for the wide use of compact QDs, as separation of QD-protein conjugates from unreacted proteins is highly inefficient and low-throughput using processes involving chromatography, electrophoresis, and centrifugation.

We investigated the nonspecific and specific binding of P-IM-coated QDs on fixed cells. The OEG surface was critical for minimizing nonspecific binding, which can be seen by comparing fluorescence images of cells exposed to QDs coated with P-IM or a P-IM-COOH polymer that was nearly identical but for which OEG was replaced with carboxylic acids. Using click chemistry, we conjugated (QD)P-IM-$N_3$ to an antibody (Ab) against the epidermal growth factor receptor (EGFR), validated by a gel shift. The QDs were added to A431 cells expressing human EGFR, and bound selectively to the membrane region, unlike QDs conjugated to an isotype control antibody.

Quantum dots coated with P-IM also efficiently self-assembled with proteins expressed as fusions to His-tag, similarly to previous reports using QDs coated with small ligands. It is surprising that this process occurs efficiently for QDs with a polymeric shell and dense OEG layer. QDs were conjugated to proteins (Protein A) using this mechanism. Protein binding decreased the gel mobility of QDs with multiple protein conjugate bands observed, and the unconjugated QDs were largely depleted at a Protein:QD ratio of 4:1. Specificity for attachment through the His-tag was verified by control experiments in which Protein A was not labelled with a His-tag, showing no change in gel mobility of the QDs.

Figure 9A:
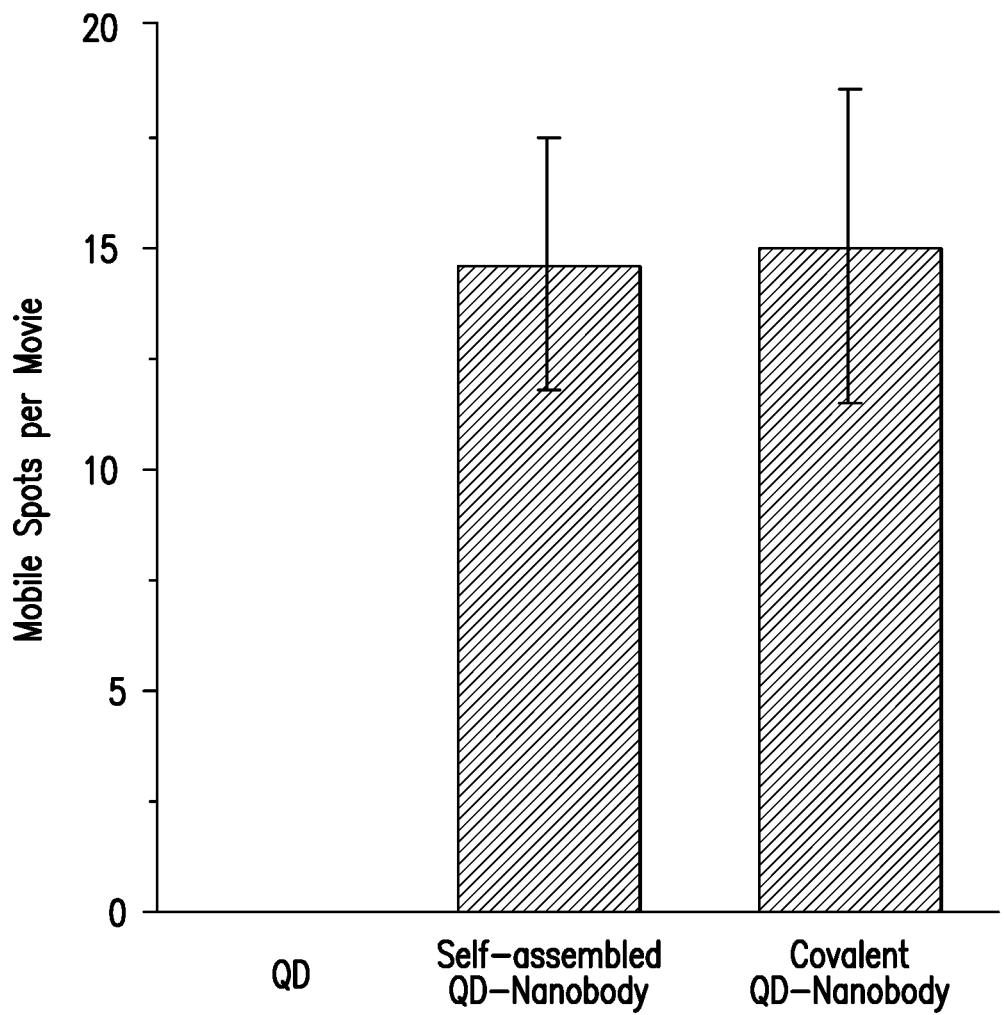
FIGS. 9a and 9b. P-IM-coated QDs conjugate through His-tag linkers, retain protein function, and can be used for single-molecule imaging of motor proteins.

To verify that they retained their function such that they could be used for single-molecule dynamic imaging applications, P-IM-coated QDs was conjugated to a His-tagged protein called a nanobody, which is a small variant of an antibody. The nanobody was specific for green fluorescent protein (GFP). The QD-nanobody was mixed with a GFP-kinesin fusion protein, and a well-established single-molecule kinesin motility assay was applied to evaluate whether these QD tags are effective probes for enzymatic single-molecule analysis. Individual conjugates were readily seen through fluorescence imaging. Kinesin mobility analysis showed about 15 mobile QDs per movie for QD-nanobody conjugates compared to zero mobile QDs for samples not conjugated to nanobodies (FIG. 9a). The results were compared for self-assembled QD-nanobody conjugates with an assay that was identical, except we used QDs-nanobody conjugates prepared through covalent linkage through a PEG spacer, and the results were statistically indistinguishable (FIG. 9a).

Figure 9B:
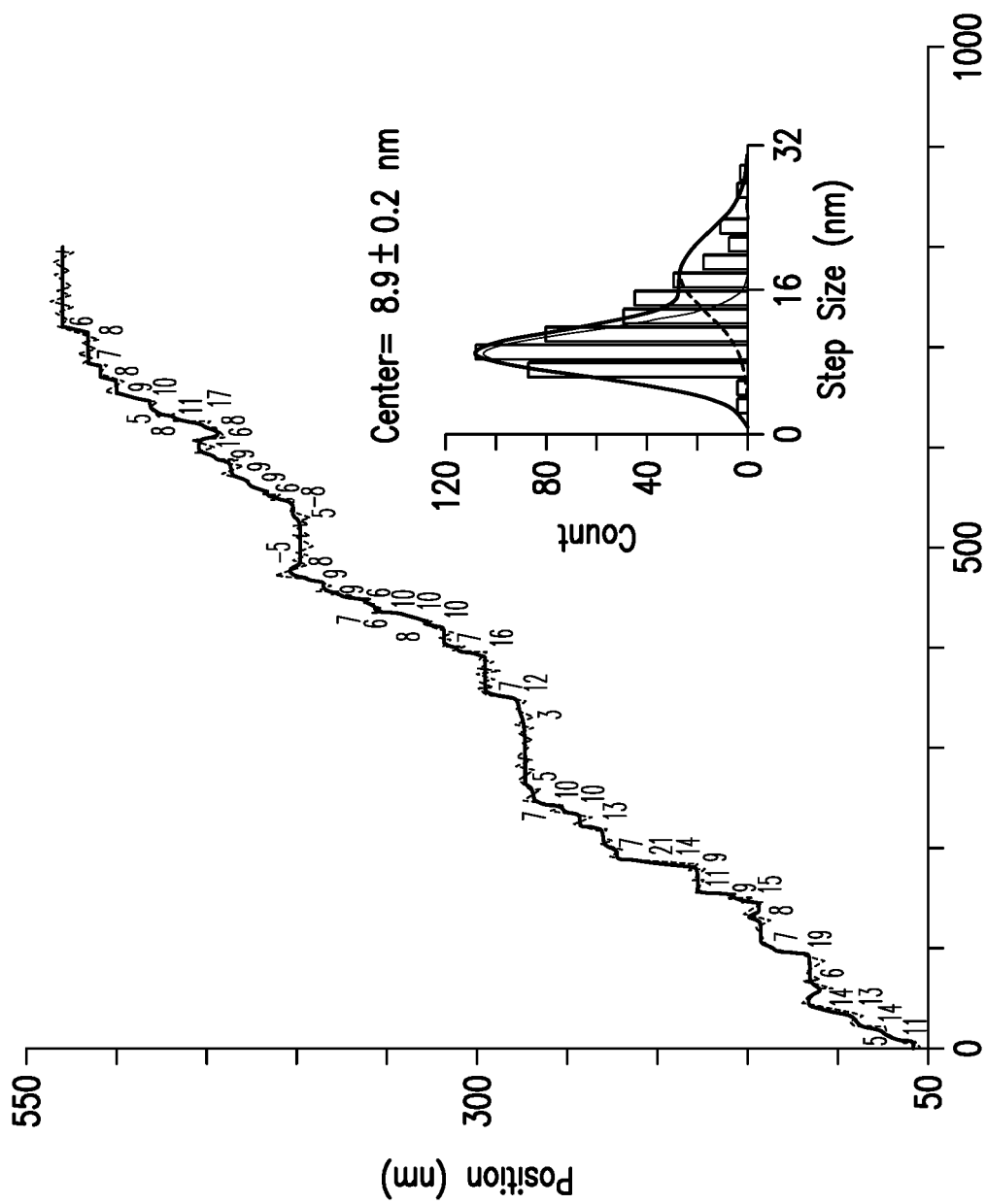
Figure 10:
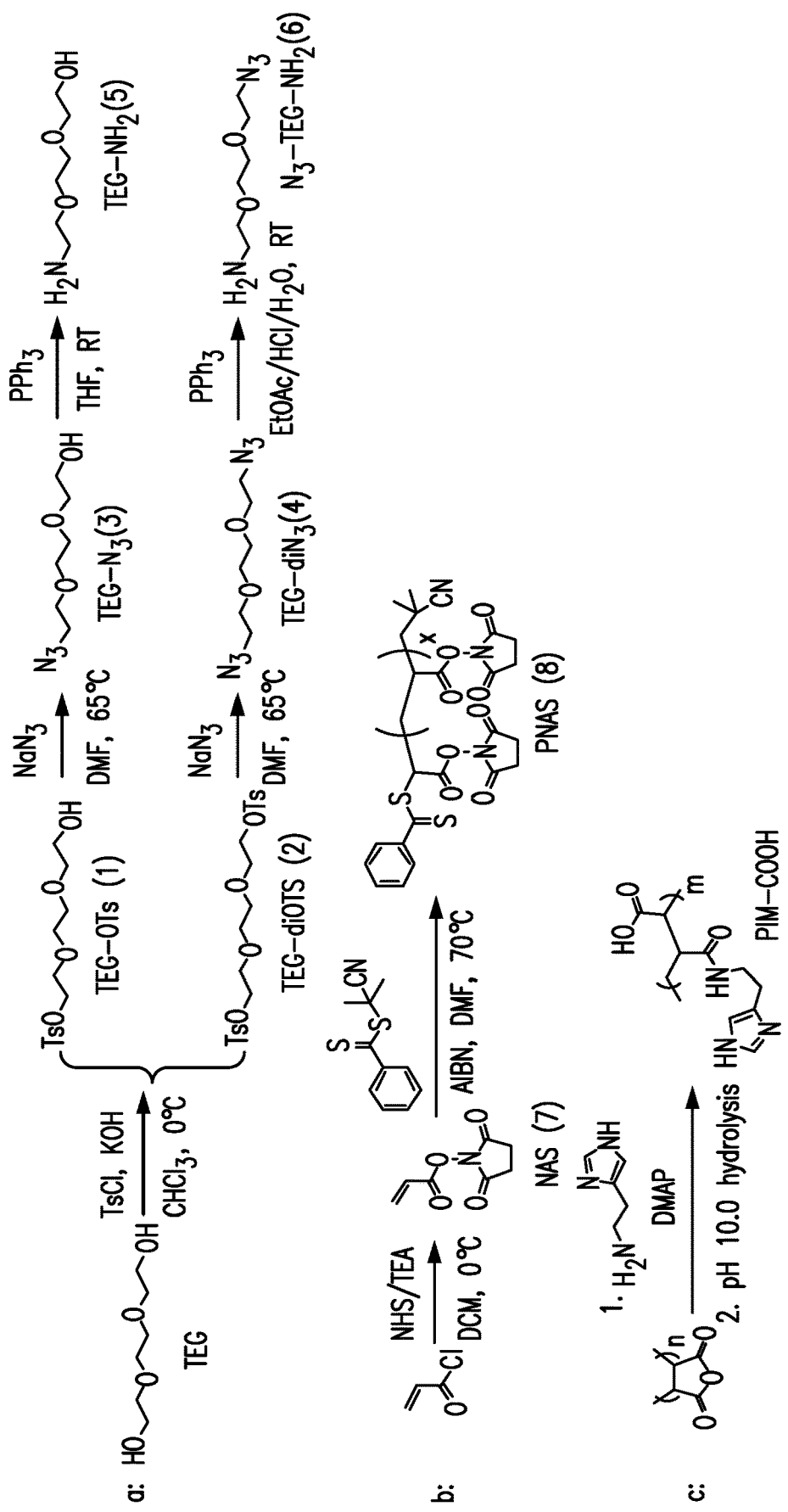
FIG. 10. Polymeric multidentate ligand synthesis. (Reaction scheme a) Synthesis of triethylene glycol derivatives. (Reaction scheme b) Preparation of pol(N-acryloy succinimide), PNAS, via RAFT polymerization. (Reaction scheme c) Synthesis of PIM-COOH.

These results demonstrate that P-IM QD probes allow nanobodies bound through His-tags to retain their affinity and do not damage the enzymatic function of kinesin, despite possibly being slightly buried in the OEG shell due to the very short linker between the nanobody and QD. Due to the very high photostability and brightness of these probes under high-power laser excitation, the step size of the kinesin motor protein was analysed with nanometer-accuracy and 100 ms time resolution (FIG. 9b). Statistical analysis showed an average step size of 8.9 nm, which is in excellent agreement with the predicted 8.3 nm per step for kinesin labelled at its center of mass position. These very compact and functional conjugates (about 12 nm diameter) are thus very suitable for high-sensitivity single-molecule imaging without interference in enzymatic processes.

Example 3—Additional Methods

Synthesis of Core/Shell CdSe/Cd$_x$Zn$_{1-x}$S QDs: CdSe cores with diameter of 2.3 nm (for QD525 and QD565) or 3.0 nm (for QD600 and QD605) were synthesized using conventional high-temperature arrested precipitation methods as previously described in the literature, see, for example, Murray et. al. *Ibm J. Res. Dev.* 2001, 45, 47-56. After purification, Cd$_x$Zn$_{1-x}$S shells were grown layer-by-layer. In a typical shell growth reaction, a purified core stock in hexane (~1 micromole) was injected into a mixed solvent of ODE (12 mL) and OLA (6 mL) in a 250 mL round bottom flask and hexane was evaporated under vacuum at 40-50° C. Then, the solution was heated under nitrogen to a temperature used for the first 0.8 ML shell growth (typically 120-130° C.). The first S precursor 0.8 monolayer (ML) was added dropwise within 5-10 min and allowed to react for ~20 min. Equal amounts of Cd/Zn precursor was added in the same manner and allowed to react for another ~20 min to complete the 0.8 ML shell growth. This cycle was repeated while gradually increasing both the Zn ratio (typically from 0.5 to 1) and the reaction temperature (typically from 130° C. to 200° C.). An aliquot (200 µL) was withdrawn using a glass microsyringe after every 0.8 ML shell growth to monitor the reaction and to measure the extinction coefficient. When the desired emission wavelength was reached, an additional injection of Zn precursor was added and the particles were annealed for ~20 min in order to render the QD surfaces metal-rich. Specific quantities used for each batch are provided in Supplementary Information. Mixtures were cooled and stored as a crude reaction mixture at −20° C. freezer until use.

Synthesis of poly(cysteamine-b-TEG)amide (P-SH). In a 7 mL vial equipped a magnetic stir bar, PNAS (synthesized as described in Gujraty et. al. *Polym. Sci., Part A: Polym. Chem.* 2008, 46, 7249-7257) (84 mg) was dissolved in dry DMF (1 mL). Monoamine triethylene glycol (HO-TEG-NH$_2$, 325 µL, 1.0 mM in dry DMF) was added and the mixture was stirred for 2 h. Cysteamine (350 µL, 0.5 mM in dry DMF) was then added and the solution was purged with N$_2$ for 5 min. The reaction was allowed to continue for 24 h at room temperature. DL-dithiothreitol (8 mg) was then added and the solution was stirred for 1 h. The solution was diluted 5-fold with an HCl aqueous solution (0.1 mM) and loaded into a dialysis bag (molecular weight cut-off, MWCO=2 kDa). The polymer was purified by dialysis in HCl solution (1 L, 0.1 mM) for 6 h and repeated 3 times. The yellow powder (51 mg) was collected using a lyophilizer (yield 68%). $^1$H NMR (d$_6$-DMSO, δ, ppm, 500 MHz): 7.52-7.82 (Ph, br), 4.57 (CH$_2$, br), 3.14-3.52 (CH$_2$, br), 2.85 (CHCH$_2$, br), 1.54-2.31 (CHCH$_2$, m), 1.22 (CH$_3$, br).

Synthesis of poly(histamine-b-TEG)amide (P-IM). In a 7 mL vial equipped a magnetic stir bar, PNAS (84 mg) was dissolved in dry DMF (1.0 mL). TEG-NH$_2$ (325 µL, 1.0 mM in dry DMF) and histamine (175 µL, 1.0 mM in dry DMF) were added and the solution was purged with N$_2$ for 5 min. The solution was stirred for 24 h at room temperature. The solution was diluted 5-fold with deionized water and loaded into a dialysis bag (MWCO=2 kDa). The polymer was purified by dialysis in deionized water for 6 h and repeated 3 times. A yellow solid product (49 mg) was collected after lyophilization (yield 51%). $^1$H NMR (d$_6$-DMSO, δ, ppm, 500 MHz): 7.50-7.93 (Ph, IM, br), 4.58 (CH$_2$, br), 3.18-3.47 (CH$_2$, br), 2.81 (CHCH$_2$, br), 1.47-2.07 (CHCH$_2$, m), 1.31 (CH$_3$, br).

Synthesis of poly(histamine-b-TEG-b-azide TEG)amide (P-IM-N$_3$). In a 7 mL vial equipped a magnetic stir bar, PNAS (84 mg) was dissolved in dry DMF (1.0 mL). Then 2-[2-(2-azido-ethoxy)-ethoxyl]-ethylamine (N$_3$-TEG-NH$_2$, 100 µL, 1.0 mM in dry DMF), TEG-NH$_2$ (225 µL, 1 mM in dry DMF) and histamine (175 µL, 1.0 mM in dry DMF) were added and the solution was purged with N$_2$ for 5 min. The solution was stirred for 24 h at room temperature and then diluted 5-fold with deionized water and loaded into a dialysis bag (MWCO=2 kDa). The polymer was purified by dialysis in deionized water for 6 h and repeated 3 times. A yellow solid product (62 mg) was collected after lyophilization (yield 56%). $^1$H NMR (d$_6$-DMSO, δ, ppm, 500 MHz): 7.45-7.93 (Ph, br), 3.21-3.47 (CH$_2$, br), 2.80 (CHCH$_2$, br), 1.51-1.93 (CHCH$_2$, m), 1.20 (CH$_3$, br).

Polymer Coating Methods: CdSe/Cd$_x$Zn$_{1-x}$S QDs in the crude reaction mixture were purified (More details can be found in SI) and the solution was centrifuged to remove possible aggregates. The general procedures for six different phase transfer methods used in this work are described as follows and additional details are listed in the Supplementary Information.

Method 1 (hydrophobic ligand surface): Hexane was removed from a dispersion of QD605 by evaporation and the nanocrystals were redispersed in CHCl$_3$. Multidentate ligands P-IM or P-SH (5 equiv of binding group per QD surface atom) dissolved in CHCl$_3$ were added under N$_2$ atmosphere. The reaction was allowed to proceed for 10 min at room temperature. Methanol was then added and the reaction was continued for 20 min under N$_2$ atmosphere. QDs were collected by precipitation with hexane. The nanocrystals were purified by dialysis (MWCO=50 kDa) to remove residual organic solvent and excess polymers, concentrated by centrifugal filtration (MWCO=50 kDa), and stored in sodium borate buffer (50 mM, pH 8.5) at room temperature.

Method 2 (S$^{2-}$ surface): An aqueous solution of (NH$_4$)$_2$S (40%) was added to a biphasic mixture of NMF and hexane containing QD605. The mixture was stirred vigorously until complete phase transfer to the NMR phase. Hexane was removed and the NMF layer containing the QDs was washed with hexane twice, followed by precipitation with ethyl acetate and centrifuged to collect the QDs. The QDs were resuspended in NMF. A solution of P-IM or P-SH in NMF was added dropwise into the solution under stirring and N$_2$ atmosphere. The reaction was allowed to proceed at room temperature for 24 h. The nanocrystals were purified and stored in the same way as Method 1.

Method 3 (Zn$^{2+}$ surface): QDs with a S$^{2-}$ surface in NMF from Method 2 were mixed with a solution of Zn(Ac)$_2$ in formamide and stirred for 5 min. The QDs were collected by precipitation from toluene and redispersed in NMF. A solution of P-IM or P-SH in NMF was added dropwise into the QD-NMF solution while stirring. The solution was bubbled with N$_2$ for 5 min and the reaction was allowed to proceed at room temperature for 24 h. The nanocrystals were purified and stored in the same way as Method 1.

Method 4 (thioglycerol surface): Hexane was removed from a dispersion of QD605 by evaporation. Pyridine was added in a $N_2$ atmosphere and the solution was stirred at 80° C. for 2 h. Then thioglycerol was added and stirred at 80° C. for an additional 2 h. Triethylamine was added after the solution was cooled to room temperature and stirred for 30 min. The QDs were precipitated by slow addition into a acetone/hexane mixture and collected by centrifugation. The obtained QDs were homogeneously dispersed in DMSO. A DMSO solution of P-IM or P-SH was added dropwise to the QDs while stirring in an $N_2$ atmosphere. The reaction was then heated to 80° C. under $N_2$ for 1.5 h. The nanocrystals were purified and stored in the same way as Method 1.

Method 5 (mPEG-SH surface): A hexane dispersion of QDs was diluted with $CHCl_3$, and a solution of mPEG-SH in $CHCl_3$ (5000 per QD) was added and stirred for 3 h at room temperature. The solvent was evaporated and the QDs were dispersed in methanol and bubbled with $N_2$ for 3 min. A methanol solution of tetramethylammonium hydroxide (TMAH, 25 wt %) was added with mPEG-SH in the same molar quantity. The reaction was allowed to proceed for 2 h at 60° C. under $N_2$ atmosphere. The QDs were collected by precipitation and redispersed in DMF. P-IM or P-SH was added dropwise into the QDs solution with stirring and in a $N_2$ atmosphere. The reaction was allowed to proceed at room temperature for 24 h. The nanocrystals were purified and stored in the same way as Method 1.

Method 6 ($OH^-$ surface): A methanol solution of TMAH (25%) was added to biphasic mixture of NMF and a hexane suspension of QD605. The suspension was stirred vigorously for 1 h until the QDs were completely transferred to the NMF phase. Hexane was removed and the NMF solution was washed with hexane twice. Residual hexane and methanol were evaporated under vacuum. A solution of P-IM or P-SH in NMF was added dropwise into the solution under stirring and $N_2$ atmosphere. The reaction was allowed to proceed at room temperature for 24 h. The nanocrystals were purified and stored in the same way as Method 1.

Further Details on Method 6

Solvent: The QD605 NMF solution obtained in Method 6 (0.2 mL, 10 μM) was diluted with DMSO (0.4 mL), NMF (0.4 mL) or methanol (0.4 mL). Then P-IM (3.8 mg, 5 equiv of surface atoms of QDs) dissolved in corresponding solvent (0.2 mL) was added while stirring in a $N_2$ atmosphere. The reaction was stirred at 70° C. for 5 h. The nanocrystals were purified and stored in the same way as Method 1.

Time: The QD605 NMF solution obtained in Method 6 (0.2 mL, 10 μM) was diluted with DMSO (0.4 mL). Then a DMSO solution of P-IM (5 equiv of surface atoms of QDs, 19 mg/mL, 0.2 mL) was added while stirring in a $N_2$ atmosphere. The reaction was stirred at 70° C. for 1 h, 2 h, or 4 h. The nanocrystals were purified and stored in the same way as Method 1.

Molar Capping Ratio: The QD605 NMF solution obtained in Method 6 (0.2 mL, 10 μM) was diluted with DMSO (0.4 mL). Then a DMSO solution of P-IM (1 equiv, 2 equiv and 5 equiv of surface atoms of QDs) was added while stirring in a $N_2$ atmosphere. The reactions were carried at 70° C. for 2 h. The nanocrystals were purified and stored in the same way as Method 1.

Temperature: The QD605 NMF solution obtained in Method 6 (0.2 mL, 10 μM) was diluted with DMSO (0.4 mL). Then a DMSO solution of P-IM (5 equiv of surface atoms of QDs, 19 mg/mL, 0.2 mL) was added while stirring in a $N_2$ atmosphere. The solution was stirred at room temperature, 70° C. or 110° C. 2 h. The nanocrystals were purified and stored in the same way as Method 1.

Synthesis of (QD525)P-IM, (QD565)P-IM and (QD605)P-IM. The synthesis procedures for (QD525)P-IM, (QD565)P-IM and (QD605)P-IM were identical except that the number of surface atoms was different between the different QDs due to different diameters. NMF solutions (0.2 mL) of hydroxide-coated QDs obtained through Method 6 (QD605, 2.0 nmol; QD565, 5.1 nmol; QD525, 8.7 nmol) were diluted with DMSO (0.4 mL). Then P-IM DMSO solution (5 equiv of surface atoms of QDs, 19 mg/mL, 0.2 mL) was added while stirring in a $N_2$ atmosphere. The solution was stirred at 110° C. for 2 h. The QDs were further purified by dialysis to remove organic solvents and unreacted polymer and concentrated by centrifugal filtration. For QD605 and QD565, the MWCO of dialysis bag and centrifugal filter was 50 kDa. For QD525 the MWCO was 30 kDa. The obtained QDs were stored in sodium borate buffer (50 mM) for use and characterization. The procedures were identical when using the P-IM-$N_3$ polymer.

Synthesis of Monodisperse and Polydisperse QDs. QD cores with 720-nm emission were chosen for this sample so that we could achieve the highest signal-to-noise ratio in single-molecule imaging experiments for hydrodynamic size analysis with maximum accuracy, and were synthesized according to our previous publication.[7b] The monodisperse and polydisperse samples were prepared using identical cores and identical procedures except using different molar capping ratios and coating temperatures during polymer attachment. For both, NMF dispersions (0.255 mL) of hydroxide-capped QDs (1 nmol) obtained through Method 6 were diluted with DMSO (0.75 mL). For monodisperse samples, a DMSO solution of P-IM (12 mg/mL, 33 μL) was added at a molar capping ratio of 1.5 while stirring under a nitrogen atmosphere. The solution was stirred at 110° C. for 2 h. For polydisperse samples, the molar capping ratio was 0.5 and the temperature was 70° C. All other conditions were identical and the QDs were purified and concentrated using the same procedure described in Method 1 above.

Conjugation of DBCO-DNA to P-IM-$N_3$-coated QDs. Dibenzocyclooctyl (DBCO) terminated oligonucleotide probe (length 90 bp) was purchased from a commercial vendor (Integrated DNA technology, Coralville, Iowa) with HPLC purified. The sequence used was /5'-DBCO-triethyleneglycol (TEG)/$(T)_{68}$ TAG CCA GTG TAT CGC AAT GAC G-3' (SEQ ID NO. 1). Azide functionalized QD565 in 50 mM sodium borate buffer was reacted with DBCO-DNA at a molar ratio of 1:1 QD:DNA. Sodium chloride at final concentration of 25 mM was added to the reaction mixture to reduce electrostatic repulsion and achieve higher conjugation to QDs. The reaction was performed at room temperature on a vibratory shaker (750 rpm). Conjugation was measured using electrophoresis in hybrid polyacrylamide-agarose gels (2% polyacrylamide and 0.5% agarose).

Hybridization of DNA-fluor to QD-DNA. Fluorescein-modified oligonucleotides (Integrated DNA technology, Coralville, Iowa) were used to confirm that DBCO DNA-conjugated QDs retained their capacity for hybridization. The sequence used was /5'-6-fluorescein amidite (FAM)/ CGTCATTGCGATACACTGGCT-3' (SEQ ID NO. 2). Briefly, An excess of DNA-fluor (15 per QD) was added to QD-DNA (prepared with a 4:1 DBCO-DNA excess, react for 72 h in 25 mM sodium chloride). Sodium chloride at a final concentration of 0.1 M was then added. The reaction was performed at room temperature for 3 h on a vibratory shaker (750 rpm). Unhybridized DNA-fluor was removed from the using a 50-kDa MWCO centrifugal filter. Conjugation was confirmed using UV-Vis absorption.

Conjugation of Streptavidin to P-IM-N$_3$-coated QDs. Streptavidin (Catalog No. 43-4302, Life Technologies, Grand Island, N.Y.) was conjugated to azide functionalized QD565 using DBCO-sulfo-NHS ester (Catalog No. A124, Click Chemistry Tools, Scottsdale, Ariz.). Briefly, Streptavidin was reacted with a 5-fold molar excess of DBCO-sulfo-NHS ester on ice for 2 h. This DBCO-SAv was purified using a centrifugal filter (MWCO=30 kDa) at 4° C. To conjugate azide-functionalized QD565 with DBCO-SAv, azide functionalized QD565 in 50 mM sodium borate was transferred to PBS using a centrifugal filter (MWCO=50 kDa) and mixed with different ratios of DBCO-SAv at 4° C. for 24 h. The reaction was quenched by adding a 50-fold molar excess of 2-azidoacetic acid (Catalog No. 763470, Sigma-Aldrich, St. Louis, Mo.) on ice for 15 minutes. The conjugation was confirmed using electrophoresis in hybrid polyacrylamide-agarose gels (2% polyacrylamide and 0.5% agarose) at 4° C.

Conjugation of Biotin-DNA to SAv-QDs. Biotin-labelled DNA (Integrated DNA technology, Coralville, Iowa) was used to confirm streptavidin conjugation to QDs. The sequence used was /5'-Biotin/(T)$_{68}$ TAG CCA GTG TAT CGC AAT GAC G-3' (SEQ ID NO. 3). Briefly, SAv-QD (1:1 molar ratio of DBCO-SAv:QD) was incubated with different ratios of biotin-DNA at 4° C. for 2 h. Conjugation was measured using electrophoresis in hybrid polyacrylamide-agarose gels (2% polyacrylamide and 0.5% agarose) at 4° C.

Conjugation of Antibodies to P-IM-N$_3$-coated QDs. Mouse anti-human EGFR antibody (Catalog No. 555996, BD Biosciences, San Diego, Calif.) and mouse IgG Isotype Control (Catalog No. 02-6502, ThermoFisher Scientific, Waltham, Calif.) were conjugated to P-IM-N$_3$-coated QDs. Briefly, sodium azide was removed from the stock Ab using a 50 kDa MWCO centrifugal filter and then reacted with a 50-fold molar excess of DBCO-sulfo-NHS ester on ice for 2 h. Unreacted reagents were removed using a centrifugal filter. P-IM-N$_3$-coated QD565 in 50 mM sodium borate were transferred to PBS using a centrifugal filter and then incubated with different ratios of DBCO-activated antibody at 4° C. for 7 h. The reaction was quenched by adding a 50-fold molar excess of 2-azidoacetic acid on ice for 15 minutes. Conjugation was confirmed using electrophoresis in hybrid polyacrylamide-agarose gels (2% polyacrylamide and 0.5% agarose).

Evaluation of Nonspecific Binding to Cells. HeLa cells (ATCC #CCL2) were cultured in Eagles' Minimum Essential Medium (EMEM) with 10% fetal bovine serum (FBS) and 1% penicillin/streptomycin (P/S) at 37° C. with 5% CO$_2$. Cells were seeded at a 5×10$^4$ cell/well density on 12-mm circular cover glass (Catalog No. 633029, Carolina) in 24 well plates and cultured for 24 h. The cells were washed three times with PBS before fixation with freshly prepared 4% paraformaldehyde (PFA, catalog no. RT 15714, Electron Microscopy Sciences, Hatfield, Pa.) for 20 min at room temperature. The cells were washed with PBS three times and permeabilized with 0.1% Triton X-100 (catalog no. T8787, Sigma-Aldrich, St. Louis, Mo.) in PBS for 20 min. The cells were washed with PBS three times and blocked with 1 wt % bovine serum albumin (BSA) for 1 h. The cells were washed with PBS three times, and 40 nM dispersions of (QD)P-IM or (QD)P-IM-COOH in 1 wt % BSA solution were added to the wells and incubated for 1 h at room temperature. Control experiments were carried out by incubating cells without QDs. The cells were washed three times with PBS to remove unbound QDs and the nuclei were stained with Hoechst 33258 dye (2 μg/mL, Thermo Scientific, Waltham, Mass.). The coverglass with cells was then mounted with 90% Glycerol in PBS on a glass slide and sealed with nail polish. The cells were imaged immediately on a Zeiss Axio Observer. Z1 inverted microscope (Zeiss, Oberkochen, Germany) with an EC Plan-Neofluar 20×/0.50 NA air microscope objective and 100 W halogen lamp excitation. Hoechst signal was imaged using a 365 nm excitation filter and 445/50 nm emission filter; QDs were imaged using a 488 nm laser excitation and 600/37 bandpass emission filter. Images from the control and QD samples were collected using the same imaging conditions.

Immunofluorescence Staining using QD-Ab Conjugates. A431 cells (ATCC #CRL-1555) were cultured in Dulbecco's Modified Eagle Medium (DMEM) supplemented with 10% FBS and 1% P/S. were seeded at a density of 50,000 cells/well in a labtek glass-bottom 8 well chamber (Thermo Scientific, Waltham, Mass.) and incubated at 37° C. with 5% CO$_2$ for 20 h. The cells were then fixed with 4% PFA for 20 minutes, permeabilized with 0.1% (v/v) Triton X-100 for 20 minutes, and blocked with 1% BSA for 1 h. The cells were then incubated with 10 nM QD565-EGFR antibody conjugate in 1% BSA at temperature for 30 minutes, and stained with 2 μg/mL of Hoechst for 10 minutes. All treatments were carried out at room temperature. The samples were imaged immediately using a 100×1.45 NA alpha Plab-Fluar oil immersion objective on a Zeiss Axio Observer Z1 inverted microscope. Hoechst signal collected as described above; QD565 signal was imaged using a 488 nm laser excitation and a 562/40 bandpass emission filter. Images from the QD565-IgG control conjugate and QD565-EGFR antibody conjugate samples were collected using the same imaging conditions.

Expression and Purification of Nanobody. The expression and purification protocol and vector information of His-tagged GFP-binding nanobody has been previously published. In short, the nanobody was expressed in BL21 cells for 4 h at room temperature, and then pelleted and lysed using 1 mg/mL lysozyme and sonication. The lysate were pelleted by centrifugation at 15,000 g for 30 minutes. The supernatant was collected and added to nickel affinity resin. The nanobody, nickel resin mixture was incubated at 4° C. for 1.5 h while shaking. Flow-through was discarded, and the nanobody was eluded using a gradient of imidazole buffer from 50 mM to 250 mM.

Conjugation of His-Tagged Protein A to QD. To conjugate His-tagged protein to P-IM-coated QDs, the QDs (1 μM) were incubated with different ratios of His-tagged Protein A (Catalog No. 6500-10, BioVision, Inc., Milpitas, Calif.) or Protein A without a His-tag (Catalog No. 21181, Thermo Scientific, Waltham, Mass.) at room temperature in 10 mM phosphate buffer (pH 7.4) for 2 hours. Conjugation was assessed by gel electrophoresis in a hybrid polyacrylamide-agarose gel (2% polyacrylamide and 0.5% agarose) at 4° C.

Conjugation of Nanobody to QD. To conjugate His-tag nanobody to P-IM-coated QDs, the QDs in borate buffer were transferred to PBS, and incubated with different ratios of His-tag nanobody at 4° C. for 4 h. Conjugation was measured using electrophoresis in hybrid polyacrylamide-agarose gels (2% polyacrylamide and 0.5% agarose).

Labeling of Kinesin and Single-Molecule Imaging of Labeled Kinesin. Truncated Kinesin-1 with a green fluorescent protein at the c-terminus (K560-GFP) was incubated with QD-nanobodies or unconjugated QDs at a 3-fold molar excess of QDs for 20 minutes on ice. An imaging chamber was assembled by creating micro-channels roughly 2 mm in width using double sided tapes on cleaned microscope slides. A coverslip coated with 5% PEG-Biotin/95% PEG was firmly mounted to the other side of the double sided tape. 10 μL of 0.5 mg/mL Streptavidin was added to the micro-channels and incubated for 5 minutes. Excess streptavidin was rinsed out of the micro-channel. 10 μL of biotinylated Hilyte488-labeled microtubule consists of roughly 25 nM tubulins in solution of BRB80-BSA (80 mM 1,4-piperazinediethanesulfonic acid (PIPES), 1 mM ethylene glycol tetraacetic acid (EGTA), 1 mM $MgCl_2$, and 8 mg/mL BSA, pH 6.8) containing 20 μM paclitaxel was added to the flow channel and allowed to bind for 5 minutes. Excess microtubules were rinsed out with BRB80-BSA containing 20 μM paclitaxel. Kinesin-QD mixture was diluted to nanomolar concentration and added to Imaging Buffer (BRB80-BSA, 1 mM tris(3-hydroxypropyl)phosphine (THP), 20 μM paclitaxel, 1 U/mL creatine kinase, 2 mM creatine phosphate, 50 nM protocatechuate-3,4-dioxygenas, 1 mg/mL protocatechuic acid) and subsequently flowed into the micro-channels containing microtubules, and allowed to incubate without any adenosine triphosphate (ATP) for 5 minutes to allow labeled kinesin to bind to the microtubules. Then 800 nM ATP in Imaging Buffer was added to the chamber to wash out the unbound kinesin and unlabeled QDs. For experiment involving measurement of step sizes, 300 nM of ATP was used instead. The sample was imaged using a custom-built objective-type total internal reflection fluorescence (TIRF) microscope. QDs were excited using a 532 nm laser. For experiments that involved measuring step sizes, a 605/15 emission filter was added to the setup. For motility experiments, movies were collected using an Andor iXon EM-CCD camera with 150 ms exposure time and EM gain of 200 for 300 frames. To discern individual step sizes, laser power was increased 4-fold, exposure time was decreased to 100 ms, and EM gain between 50 and 10.

Data Analysis of Motile Kinesin and Step Size Determination. The number of processive moving bright spots in each movie obtained at 800 nM ATP were counted and averaged to yield the number of motile kinesin per movie. For step size determination, motile spots in movies recorded at 300 nM ATP were cropped, and single-molecule fluorescence images of QDs in each frame of the movie were fit to a 2D Gaussian function to determine its center. Since kinesin travels on a single protofilament in one direction, the set of x-y coordinate obtained from Gaussian fitting was linearized to reduce its dimensionality. The tracked position as function of time is then fit using the SICstepfinder algorithm[36] to determine the step size from the recorded traces. The step sizes were collected from all traces, and Gaussian functions were used to fit the distribution of the step sizes.

Materials for Polymeric Multidentate Ligand Synthesis

Triethylene glycol (TEG, 99%), p-toluenesulfonyl chloride (TsCl, 99%), sodium azide ($NaN_3$, >99.5%), triphenyl phosphine (PPh3, >98.5%), sodium bicarbonate (NaHCO3, >99.7%), 2,2'-azobis(2-methylpropionitrile) (AIBN, 98%), histamine (97%), N-hydroxysuccinimide (NHS, 98%), Acryloyl chloride (97%), 4-(dimethylamino)pyridine (DMAP, >99%) and 2-Cyanoprop-2-yl-dithiobenzoate were purchased from Sigma-Aldrich. Silica gel (230-400 mesh) was purchased from Silicycle Inc, Canada. Behenic acid (BAc, 99%) was obtained from MP Biomedicals. Tetradecylphosphonic acid (TDPA, >99%) was purchased from PCI Synthesis. Poly(maleic anhydride) (MW=5 kDa) was purchased from PolySciences, Inc, USA. Solvents including tetrahydrofluran (THF), chloroform ($CHCl_3$), hexane, toluene, methanol (MeOH), and acetone were purchased from various suppliers including Acros Organics, Fisher Scientific, Macron Fine Chemicals. Milli-Q water was used throughout. Unless specified, all the other chemicals and solvents were purchased from Sigma-Aldrich and used without further purification.

Materials for Quantum Dot Synthesis 1-octadecene (ODE, 90% tech.), oleylamine (OLA, 80-90% C18-content) and oleic acid (Oac, 90% tech.) were obtained from Acros Organic. Trioctylphosphine oxide (TOPO, 99%) and trioctylphosphine (TOP, 97%) were purchased from Strem Chemicals (Newburyport, Mass., USA). Anhydrous cadmium chloride ($CdCl_2$, 99.99%), and zinc acetate ($Zn(Ac)_2$, 99.98%) were obtained from Alfa Aesar. Cadmium acetate hydrate ($Cd(Ac)_2.H_2O$, 99.99+%), selenium dioxide ($SeO_2$, 99.9%), selenium powder (Se, ~100 mesh, 99.99%), sulfur powder (S, 99.98%), diphenylphosphine (DPP, 98%), 1,2-hexadecanediol (HDD, 97%) were purchased from Sigma-Aldrich.

Materials for Phase Transfer, Ligand Exchange and Gel Electrophoresis

Thioglycerol (97%), triethylamine (TEA, >99%), ammonium sulfide solution (($NH_4)_2S$, 40-48 wt. % in water), zinc acetate (($Zn(Ac)_2$, >99.99%), formamide (>99.5%), acylamide/N,N'-methylenebisacrylamide (19:1, 40% mix solution in water), tetramethylammonium hydroxide solution (TMAH, 25 wt. % in methanol), N-methylformamide (NMF, >99%), fluorescein (fluorescence grade) were purchased from Sigma-Aldrich. Agarose was purchased from Fisher Scientific. N,N,N',N'-tetramethylethylenediamine (TMEDA) was obtained from Bio-Rad laboratories Inc. mPEG-SH (MW 356.5 Da) was purchased from POLYPURE (Catalog No. 11156-0695, Norway).

Materials for Immunofluorescence and Single Molecule Imaging

DBCO-sulfo-NHS ester was purchased from Click Chemistry Tools. Azidoacetic acid and Triton-X 100 were obtained from Sigma-Aldrich. All oligonucleotides were purchased from Integrated DNA Technologies. Streptavidin was purchased from Life Technologies. Mouse anti-human EGFR antibody was purchased from BD Biosciences. Mouse IgG Isotype control, Hoechst 33258 dye, Protein A without a His-tag, and 8-well labtek chambers were purchased from ThermoFisher Scientific. Paraformaldehyde was obtained from Electron Microscopy Sciences. Histagged Protein A was purchased from BioVision, Inc.

Synthesis of Monotosyloxy Triethylene Glycol (TEG-Ots, 1) and Ditosyloxy Triethylene Glycol (TEG-diOTs, 2)

In a 500 mL round-bottom flask, triethylene glycol (TEG, 15.0 g, 0.1 mol) and tosyl chloride (28.5 g, 0.15 mol) were dissolved in $CHCl_3$ (250 mL) and KOH powder (8.4 g, 0.15 mol) was added in five portions at 0° C. The suspension was stirred for 1.4 h (the reaction was monitored via thin layer chromatography, TLC, until complete disappearance of TEG) and then washed with cold deionized (DI) water (100 mL×2) and cold saturated brine (30 mL). The $CHCl_3$ layer was dried over anhydrous $Na_2SO_4$ and the solvent was removed by rotary evaporation under vacuum. After purification by silica gel chromatography (ethyl acetate/hexane v/v=1:9) and evaporation of the solvent by vacuum, monotosyloxy triethylene glycol (1) (17.1 g, yield 60%) was obtained as a colorless liquid and ditosyloxy triethylene glycol (2) (13.6 g, yield 30%) was obtained as a white solid.

Monotosyloxy triethylene glycol (1) $^1$H NMR ($CDCl_3$, δ, ppm, 500 MHz): 7.82 (d, 2H, ArH), 7.36 (d, 2H, ArH), 4.19 (t, 2H, TsO—$CH_2CH_2$—), 3.71 (m, 4H, TsO—$CH_2CH_2$—, —$OCH_2CH_2OH$), 3.62 (m, 4H, —$OCH_2CH_2O$—), 3.59 (t, 2H, —$CH_2CH_2OH$), 2.46 (s, 3H, Ar—$CH_3$), 2.12 (br, 1H, —OH). $^{13}$C NMR (CDCl$_3$, δ, ppm, 500 MHz): 145.3, 133.0, 130.2, 128.0 (Ar), 72.8, 70.8, 70.4, 69.6, 68.8, 61.9 (—CH$_2$—), 21.9 (—CH$_3$).

Ditosyloxy triethylene glycol (2) $^1$H NMR (CDCl$_3$, δ, ppm, 500 MHz): 7.78 (d, 2H, ArH), 7.35 (d, 2H, ArH), 4.14 (t, 2H, TsO—CH$_2$CH$_2$—), 3.66 (t, 2H, TsO—CH$_2$CH$_2$—), 3.52 (br, 4H, —OCH$_2$CH$_2$O—), 2.44 (s, 3H, Ar—CH$_3$). $^{13}$C NMR (CDCl$_3$, δ, ppm, 500 MHz): 145.2, 133.2, 130.1, 128.2 (Ar), 71.1, 69.6, 69.0 (—CH$_2$—), 21.9 (—CH$_3$).

Synthesis of Monoazide Triethylene Glycol (TEG-N$_3$, 3)

In a 100 mL round-bottom flask, Monotosyloxy triethylene glycol (12.0 g, 40 mmol) and NaN3 (5.2 g, 80 mmol) were dissolved in DMF (30 mL). The reaction was allowed to proceed for 24 h at 65° C. under N$_2$ atmosphere. After cool to room temperature, DI water (50 mL) was added and the solution was extracted with ethyl acetate (100 mL×2). The organic layer was washed with DI water (100 mL×2) and cold saturated brine (30 mL). The organic solvent was dried over Na$_2$SO$_4$, filtered, and evaporated under vacuum. The residue was then purified by flash silica gel chromatography (ethyl acetate) to give compound 3 (6.3 g, yield 90%) as a yellowish oil. $^1$H NMR (CDCl$_3$, δ, ppm, 500 MHz): 3.71 (t, 2H, —OCH$_2$CH$_2$OH), 3.66 (br, 6H, —OCH$_2$CH$_2$O—, —OCH$_2$CH$_2$N$_3$), 3.59 (t, 2H, —OCH$_2$CH$_2$OH), 3.38 (t, 2H, —OCH$_2$CH$_2$N$_3$); $^{13}$C NMR (CDCl$_3$, δ, ppm, 500 MHz): 72.6, 70.8, 70.6, 70.2, 61.9.

Synthesis of Diazide Triethylene Glycol (TEG-diN$_3$, 4)

The synthesis procedure is similar that for 3. In a 100 mL round-bottom flask, Ditosyloxy triethylene glycol (11.0 g, 24 mmol) and NaN$_3$ (5.3 g, 96 mmol) were dissolved in DMF (30 mL). After the reaction, the residue was purified by flash silica gel chromatography (ethyl acetate/hexane 1:1) and a yellowish oil (4.2 g, yield 87%) was obtained. $^1$H NMR (CDCl$_3$, δ, ppm, 400 MHz): 3.66 (m, 8H, —OCH$_2$—), 3.37 (t, 2H, —CH$_2$N$_3$); $^{13}$C NMR (CDCl$_3$, δ, ppm, 400 MHz): 70.9, 70.4, 50.9.

Synthesis of Monoamine Triethylene Glycol (TEG-NH$_2$, 5)

In a 100 mL round-bottom flask, monoazide triethylene glycol 3 (6.2 g, 35.4 mmol) and triphenyl phosphine (10.2 g, 262 mmol, 1.1 eq) were dissolved in dry THF (40 mL) in an ice bath. The mixture was allowed to slowly rise to room temperature. The reaction was monitored by TLC (methanol/CHCl$_3$=1:10) until 3 was entirely consumed. The reaction mixture was diluted with DI water (30 mL) and washed with diethyl ether (30 mL×3). Then saturated NaHCO$_3$ (20 mL) was added and the solution was extracted with CHCl$_3$ (50 mL×3). The organic solvent was dried over Na$_2$SO$_4$, filtered, and evaporated under vacuum to obtain compound 5 as a pale yellow oil (4.8 g, yield 91%). $^1$H NMR (CDCl$_3$, δ, ppm, 400 MHz): 4.89 (s, 1H, —OH), 3.52-3.70 (m, 10H, —OCH$_2$—); $^{13}$C NMR (CDCl$_3$, δ, ppm, 400 MHz): 73.2, 72.9, 70.6, 70.4, 61.9, 41.7.

Synthesis of 2-[2-(2-azido-ethoxy)-ethoxyl]-ethylamine[1] (N3-TEG-NH2, 6)

In a 250 mL round-bottom flask equipped with a 125 mL funnel, triphenyl phosphine (5.24 g, 20 mmol) in ethyl acetate (30 mL) was slowly added dropwise to 4 (4.20 g, 18.1 mmol) in ethyl acetate/HCl 1 M (30/37 mL) at room temperature with vigorous stirring. The reaction was allowed to proceed for 12 h and the ethyl acetate layer was removed. The aqueous layer was washed twice with ethyl acetate (20 mL×3) and adjusted to pH 14 with NaOH. The resulting aqueous solution was extracted with CHCl$_3$ (50 mL×3) and the organic solvent was dried over Na$_2$SO$_4$ and evaporated under vacuum to yield compound 6 (2.68 g, yield 85%). $^1$H NMR (CDCl$_3$, δ, ppm, 500 MHz): 3.56 (m, 6H, —OCH$_2$—), 3.46 (t, 2H, —OCH$_2$CH$_2$N$_3$), 3.30 (t, 2H, —OCH$_2$CH$_2$N$_3$), 2.86 (br, 2H, —NH$_2$), 2.81 (t, 2H, —CH$_2$NH$_2$); $^{13}$C NMR (CDCl$_3$, δ, ppm, 400 MHz): 72.6, 70.7, 70.4, 70.2, 50.9, 41.5.

Synthesis of N-acryloxysuccinimide (NAS, 7)

N-acryloxysuccinimide 7 was synthesized according to literature protocols that were slightly modified.[2] In a 250 mL flask, N-hydroxysuccinimide (5.87 g, 50 mmol) and dry triethylamine (7 mL, 50 mmol) were dissolved in dry dichloromethane (100 mL). Acryloyl chloride (4.6 mL, 55 mmol) was slowly injected into the solution in an ice bath and the reaction was allowed to proceed for 5 h. The suspension was filtered and washed twice with cold DI water (30 mL×2) and cold saturated brine (30 mL). The organic layer was dried over anhydrous Na$_2$SO$_4$ and the filtrate was condensed to 20 mL by rotary evaporation under vacuum. A white solid was obtained by adding ethyl acetate (50 mL). The product was further purified by silica gel chromatography with DCM/ethyl acetate (3:1) as an eluent (6.6 g, 78% yield). $^1$H NMR (CDCl$_3$, δ, ppm, 500 MHz): 6.64 (d, 1H, CH$_2$=CH—), 6.13-6.29 (m, 2H, CH$_2$=CH—), 2.78 (br, 4H, —CH$_2$CH$_2$—); $^{13}$C NMR (CDCl$_3$, δ, ppm, 400 MHz): 169.5 (CHC=OO), 161.5 (CH$_2$C=ON), 136.9 (CH$_2$=CH—), 123.7 (CH$_2$=CH—), 25.8 (—CH$_2$—).

Synthesis of Polymer (PNAS, 8)

Polymerization of monomer 7 was performed according to literature protocols.[3] In a 20 mL Schlenk tube, NAS 7 (1.01 g, 6.0 mmol), 2-cyanoprop-2-yl-dithiobenzoate (44 mg, 0.2 mmol) and AIBN (3.2 mg, 0.02 mmol) were dissolved in anhydrous DMF (1 mL). The [M]/[CTA]/[Initiator] ratio was kept at 30:1:0.1. The Schleck tube was filled with argon and then evacuated (with an oil pump) in a dewar filled with liquid nitrogen. The argon/vacuum process was repeated three times. The solution was then charged with argon and allowed to react at 70° C. After 2 h, the reaction was stopped by immersing the tube in liquid nitrogen. DMF (5 mL) was added to dissolve the product, which was precipitated with acetone (40 mL) and recovered by centrifugation. The polymer was further washed several times with anhydrous acetone and dried under vacuum (0.81 g, yield 80%). $^1$H NMR (d$_6$-DMSO, δ, ppm, 500 MHz): 7.36-7.91 (Ph, m), 3.10 (CH, br), 2.76 (CHCH$_2$, br), 2.04 (CH$_2$CH$_2$, br), 1.28 (CH$_3$, br).

Synthesis of P-IM-COOH 100 mg of Poly(maleic anhydride) (1 mmol anhydride groups) was dissolved in 0.8 mL of anhydrous DMSO containing 2 mg of DMAP. 40 mg histamine (0.35 mmol) in 0.2 mL of anhydrous DMSO was added into above solution. The reaction mixture was stirred at room temperature for about 12 hours before diluted with 4 mL of NaOH solution (pH 10.0). After 24 hour hydrolysis, the reaction solution was purified by dialysis membrane with MWCO=1 kDa. Solid powder product was obtained after 40yophilisation (50 mg, yield 40%). $^1$H NMR (D$_2$O, δ, ppm, 500 MHz): 7.7-8.3 (Imidaozle-protons), 6.8-7.2 (Imidaozle-protons), 0.2-3.8 (br).

Quantum Dot Synthesis

QD525, QD565, QD600 and QD605 were prepared by following the methods described by Smith et al Biorg. Med. Chem. 2007, 15, 6474-6488, with some modifications. First, CdSe cores with ~2.3 nm (for QD525 & QD565) or ~3.0 nm (for QD600 & QD605) in diameter were synthesized by utilizing conventional colloidal syntheses.[1,2] Then, Cd$_x$Zn$_{1-}$ $_x$S shells were grown layer-by-layer over the core until reaching the desired emission spectrum.

CdSe Core Synthesis

Diphenylphosphine Selenide (DPPSe) Synthesis.

DPPSe was synthesized by reacting DPP with Se powder in 1:1 molar ratio under nitrogen at room temperature.

Cadmium Behenate (Cd(Bac)$_2$) Synthesis.

Cd(Bac)$_2$ was prepared using a literature method.[4] CdCl$_2$ (5 mmol) was dissolved in methanol (200 mL) and filtered to remove any undissolved material, then transferred to a 500-mL dropping funnel. Bac (15 mmol) was added to a mixed solvent of methanol (1.25 L) and chloroform (150 mL) with the addition of TMAH (25 wt. % in methanol, ~8 mL). The mixture was stirred for >1 h until the white Bac powder was completely dissolved and the solution was filtered to yield a clear and colorless solution. While vigorously stirring the Bac solution in a 2-L beaker, CdCl$_2$ solution was added dropwise into the center of the liquid vortex. The entire CdCl$_2$ solution was added in ~1 h then the mixture was stirred for an additional 1 h. Cd(Bac)$_2$ was collected by vacuum filtration and washed three times with methanol (150-200 mL per wash) on a filter funnel. The product was dried on the funnel for several hours and then dried under vacuum at ~50° C. overnight.

2.3 nm CdSe—CdO (0.6 mmol), TDPA (1.33 mmol), and ODE (27.6 mL) were mixed in a 250-mL round bottom flask and heated to ~320° C. under nitrogen until the solution became clear and colorless. The temperature was decreased to 300° C. and HAD (7.1 g) was added. Then, a Se precursor containing Se dissolved in TOP (1 M, 3 mL), DPPSe (52.5 mg), and TOP (4.5 mL) was swiftly injected into the Cd solution while vigorous stirring. The heating mantle was removed 30 s after injection and the solution was rapidly cooled with a stream of air. QDs were purified by precipitation with methanol and acetone and then dispersed in hexane to be stored as a stock solution.

3.0 nm CdSe—Cd(Bac)$_2$ (1 mmol), SeO$_2$ (1 mmol), HDD (1 mmol), and ODE (20 mL) were mixed in a 250-mL round bottom flask and dried under vacuum at ~100° C. for 2 hours. Then the temperature was raised to 230° C. at a rate of ~20° C./min under nitrogen. After reaching 230° C., the temperature was maintained for 15 min. After the solution was cooled to ~110° C., the QDs were purified by diluting the solution with chloroform (10 mL) containing Oac (1 mL) and OLA (0.6 mL) then precipitating by adding a mixed solvent of methanol (15 mL) and acetone (15 mL). QDs were redispersed in hexane and extracted twice with methanol followed by precipitating with excess methanol. Finally, QDs were dispersed in hexane and stored as a stock solution.

Core/Shell CdSe/Cd$_x$Zn$_{1-x}$S Synthesis

Cd precursor solution—Cd(Ac)$_2$·H$_2$O (1 mmol) was dissolved in OLA (10 mL, 0.1 M) at ~100° C. until it became a clear solution.

Zn precursor solution—Zn(Ac)$_2$ (1 mmol) was dissolved in OLA (10 mL, 0.1 M) at ~100° C. until it became a clear solution.

S precursor solution—Elemental sulfur (1 mmol) was dissolved in OLA (0.1 M) at ~100° C. until it became a clear solution.

Layer-by-layer shell growth—A Cd$_x$Zn$_{1-x}$S shell was grown in increments of 0.8 monolayer (ML) or less instead of 1 ML to suppress homogeneous nucleation of shell materials. In a typical reaction, a purified core stock in hexane (1 μmol) was injected into the mixed solvent of ODE (12 mL) and OLA (6 mL) in a 250-mL round bottom flask and hexane was evaporated under vacuum at 40-50° C. Then, the solution was heated under nitrogen to the temperature used for the first 0.8 ML of shell growth (typically 120-130° C.). The first S precursor (0.8 ML) was added dropwise in 5-10 min and allowed to react for 20 min. An equal molar quantity of Cd$_x$Zn$_{1-x}$ precursor (x:1-x mixture of Cd and Zn precursors) was added in the same manner and allowed to react for another 20 min to complete the 0.8 ML shell growth. This cycle was repeated while gradually increasing the Zn content (reducing x) and raising the reaction temperature. An aliquot (200 μL) was withdrawn using a glass syringe after every 0.8 ML shell growth to monitor the reaction and to measure the extinction coefficient. When the desired emission wavelength was reached, an additional portion of Zn (typically enough to grow 0.8 ML) was added and the particles were annealed for 20 min in order to render the surface Zn-rich. Finally, the reaction was quenched by removing the heating mantle. These crude reaction mixtures were stored in a freezer at −20° C. until use. Detailed reaction conditions and shell compositions of QD525, QD565, QD600 and QD605 are summarized in the Table 3.

TABLE 3

Synthesis conditions for QDs

| Sample | Core | Shell | Reaction temperature | $\lambda_{Abs}$[a] (nm) | $\lambda_{Em}$[b] (nm) | FWHM[c] (nm) |
|---|---|---|---|---|---|---|
| QD525 | CdSe d = 2.3 nm | Cd$_{0.5}$Zn$_{0.5}$S 0.8 ML/ Cd$_{0.2}$Zn$_{0.8}$S 0.8 ML/ ZnS 0.4 ML | 120-140° C. 140-170° C. 170-190° C. | 509 | 524 | 32 |
| QD565 | CdSe d = 2.3 nm | CdS 0.8 ML/ Cd$_{0.5}$Zn$_{0.5}$S 0.8 ML/ ZnS 1.2 ML | 120-140° C. 140-170° C. 170-190° C. | 557 | 571 | 33 |
| QD600 | CdSe d = 3.0 nm | CdS 3.2 ML (0.8 ML × 4)/ Cd$_{0.5}$Zn$_{0.5}$S 0.8 ML/ ZnS 0.7 ML | 130-190° C. 190-200° C. 190-200° C. | 588 | 600 | 27 |
| QD605 | CdSe d = 3.0 nm | CdS 3.2 ML (0.8 ML × 4)/ ZnS 1.5 ML (0.8 ML + 0.7 ML) | 130-190° C. 190-200° C. | 591 | 603 | 27 |

[a]$\lambda_{Abs}$: absorbance wavelength at first exciton peak.
[b]$\lambda_{Em}$: emission wavelength.
[c]FWHM: full width at half-maximum of emission peak Quantum dot purification, quantum yield calculation, and gel electrophoresis.

Quantum Dots Purification and Quantum Yield Calculation

A stock suspension of QDs (2 mL) was diluted with chloroform (2 mL) in a 15 mL tube. Acetone (8 mL) was added dropwise while mixing on a vortex. The QDs were isolated by centrifugation at 7000×g for 5 min and then dispersed in hexane (7 mL). Methanol (2 mL) was added to extract the hexane solution and the biphasic mixture was vigorously mixed. The methanol phase was discarded. The QD dispersion was diluted with hexane (5 mL) and extracted with methanol (2 mL). The biphasic mixture was centrifuged (7000×g, 10 min) and the hexane phase was transferred to a 15 mL glass vial. The UV absorbance (A) was measured and used to calculate the molar concentration of the quantum dots (C) using the following formula:

$$C = \frac{A}{\varepsilon \times l}$$

Here ε represents absorption extinction coefficient, l is the path length of a quartz cuvette.

Details on quantum yield calculations can be found in our previous work, see Lim et. al., *Nat. Commun.* 2015, 6, 8210.

Gel Electrophoresis of QDs

In a 50 mL tube, an aqueous acrylamide/N,N'-methylenebisacrylamide solution (2 mL) was mixed with DI water (18 mL) and sodium borate buffer (10×, 5 mL), and the mixture was heated to 55° C. for 5 min in a warm water bath. In another 50 mL conical flask, agarose (0.25 g) was suspended in DI water (25 mL) and dissolved by heating in a microwave oven for 1 min, then mixed for 1 min and allowed to cool for 2 min. The first solution was then added and the solution was mixed for 1 min. An aqueous solution of ammonium persulfate (251 μL, 0.1 g/mL) and TMEDA (20 μL) was added to this solution and mixed by gently shaking. The solution was added to a gel casting tray and was allowed to gel for 1 h. Electrophoresis was performed at 120 V for 30 min.

Coating Methods for Polymeric Ligands

Method 1 (Hydrophobic Ligand Surface)

This method is based on previously reported methods in the literature.[6] A purified hexane suspension of QD605 (0.2 mL, 2 nmol) was transferred to a 7 mL vial. The solvent was removed under vacuum and redissoved in $CHCl_3$ (0.2 mL). A chloroform solution of P-IM or P-SH (5 eq of surface atoms of QDs, in 0.2 mL) was added and the reaction was allowed to proceed for 10 min at room temperature.

Methanol (0.4 mL) was added and the reaction was allowed to proceed for an additional 20 min. For P-SH, a 25% methanol solution of tetramethylammonium hydroxide (TMAH, 5 μL) was added and the vial was filled with $N_2$.

The solution was centrifuged at 7000 g for 10 min and the QDs were precipitated with the addition of hexane (30 mL). The QDs were collected by centrifugation at 5000×g for 5 min and redispersed in an aqueous solution of NaOH (1 mM, 2 mL).

The solution was loaded in a dialysis bag (MWCO 50 kDa) immersed in an aqueous solution of NaOH (1 mM). The dialysis solution was replaced 4 times over 1 h. The QD dispersion was then concentrated using a 15 mL centrifugal filter (MWCO 50 kDa) and diluted with sodium borate buffer (50 mM). This dilution and concentration process was repeated 4 times. The final solution was centrifuged at 7000 g for 10 min to remove potential aggregates.

Method 2 ($S^{2-}$ Surface)

This method is based on previously reported methods in the literature to generate QDs with sulphide-terminated surfaces. A pure hexane suspension of QD605 (0.2 mL, 2 nmol) was mixed with NMF (0.5 mL) in a 7 mL glass vial equipped with a magnetic stirbar. A 40% aqueous solution of $(NH_4)_2S$ (3 μL) was added. The biphasic mixture was stirred vigorously for 5 min until complete transfer of the QDs to the NMF phase.

The hexane phase was removed and the NMF phase was washed with hexane twice, followed by precipitation with ethyl acetate (8 mL) and centrifugation at 5000×g for 5 min to collect the QDs. The QDs were redispersed in NMF (0.8 mL).

P-IM or P-SH (5 eq of surface atoms of QDs) dissolved in NMF (0.1 mL) was added dropwise to the QDs suspension while stirring. For P-SH, a 25% TMAH solution in methanol (5 μL) was added. The solution was bubbled with $N_2$ for 5 min and the reaction was allowed to proceed at room temperature for 24 h. Potential aggregates were removed by centrifugation at 7000×g for 10 min.

An aqueous solution of NaOH (1 mM, 1 mL) was slowly added and the solution was stirred for 10 min. The solution was loaded in a dialysis bag (MWCO 50 kDa) immersed in an aqueous solution of NaOH (1 mM). The dialysis solution was replaced 4 times over 1 h. The QD dispersion was then concentrated using a 15 mL centrifugal filter (MWCO 50 kDa) and diluted with sodium borate buffer (50 mM). This dilution and concentration process was repeated 4 times. The final solution was centrifuged at 7000 g for 10 min to remove potential aggregates.

Method 3 ($Zn^{2+}$ Surface)

Steps 1 and 2 from Method 2 were followed to generate sulphide-terminated QDs in NMF.

A solution of $Zn(Ac)_2$ in formamide (26 μL, 0.1M) was added and the solution was stirred for 5 min. The solution was poured into toluene (8 mL) and centrifuged at 5000×g for 5 min to collect the QDs. The QDs were redispersed in NMF (0.5 mL). Potential aggregates were removed by centrifugation at 7000 g for 10 min.

Steps 3 and 4 from Method 2 were followed for polymer coating and purification.

Method 4 (Thioglycerol Surface)

This method is based on previously reported methods in the Smith and Nie, J Vis Exp 2012, e4236. A purified hexane suspension of QD605 (1 mL) was transferred to a 100 mL three neck flask equipped with a stirbar and hexane was removed under vacuum. The flask was filled with $N_2$ and then evacuated with an oil pump, and this process was repeated three times.

Pyridine (1 mL) was added under an $N_2$ atmosphere and the temperature was raised to 80° C. The reaction was allowed to proceed at 80° C. for 2 h.

Thioglycerol (0.5 mL) was added to the solution and the mixture was stirred at 80° C. for 2 h. The solution was cooled to room temperature and triethyl amine (TEA, 0.05 mL) was added to deprotonate thioglycerol. The solution was stirred for 30 min.

The solution was slowly added into an acetone/hexane mixture (5 mL/5 mL) and vortexed. The precipitate was collected by centrifugation (5000 g, 5 min), washed with acetone (5 mL), and centrifuged again (5000 g, 5 mins). The QDs were dispersed in DMSO (2 mL) with bath sonication and centrifuged at 7000 g for 10 min. The QD concentration was measured and diluted to 1 μM with DMSO.

P-IM or P-SH (5 eq of surface atoms of QDs) dissolved in DMSO (0.1 mL) was added dropwise to the QDs suspension (0.2 mL, 2 nmol) while stirring. The vial was evacuated for 5 min and then filled with $N_2$; this process was repeated 3 times. The solution was then heated to 80° C. and the reaction was allowed to proceed for 1.5 h. Potential aggregates were removed by centrifugation at 7000×g for 10 min. Step 4 from Method 2 was followed for purification.

Method 5 (mPEG-SH Surface)

A pure hexane suspension of QD605 (0.2 mL, 2 nmol) was diluted with chloroform (0.5 mL), and 5000 molar equiv of mPEG-SH (10 μmol, 3.56 mg in 100 μL $CHCl_3$) was added. The solution was stirred for 3 h at room temperature.

The solvent was evaporated and the QDs were dispersed in methanol (0.5 mL) and bubbled with $N_2$ for 3 min. A TMAH solution (10 μmol, 4.4 μL in methanol) was added and the solution was bubbled with $N_2$ for 1 min. The solution was heated to 60° C. and the reaction was allowed to proceed for 2 h.

The reaction solution was cooled to room temperature and hexane (1 mL) was added. If a biphasic mixture formed, $CHCl_3$ (0.5 mL) was added to homogenize the phases, and hexane was added until the QDs precipitated (typically 6 mL). The solution was centrifuged at 5000×g for 5 min and the QDs were recovered and dispersed in DMF (1 mL). The QDs were centrifuged at 7000×g for 10 min to remove potential aggregates.

P-IM or P-SH (5 eq of surface atoms of QDs) dissolved in DMF (0.1 mL) was added dropwise to the QDs suspension while stirring. For P-SH, a 25% TMAH solution in methanol (5 μL) was added. The solution was bubbled with $N_2$ for 5 min and the reaction was allowed to proceed at room temperature for 24 h. Potential aggregates were removed by centrifugation at 7000 g for 10 min. Step 4 from Method 2 was followed for purification.

Method 6 ($OH^-$ Surface)

This method is based on previously reported methods with a slight modification to generate QDs with hydroxide ion-coated surfaces, Nag et. al. J Am Chem. Soc 2011, 133; 10612-10620. A pure hexane suspension of QD605 (0.2 mL, 2 nmol) was mixed with NMF (0.5 mL) in a 7 mL glass vial equipped with a magnetic stirbar. TMAH (52 μL, 100 eq of surface atoms of QDs) was added to displace the nonpolar ligands and phase transfer the QDs from hexane to NMF. The biphasic suspension was stirred vigorously for 1 h until the phase transfer process was complete.

The hexane phase was removed and the NMF dispersion of QDs was washed with hexane twice while stirring for 5 min. Residual hexane was then removed under vacuum. The QDs were centrifuged at 7000 g for 10 min to remove potential aggregates and diluted with anhydrous DMSO (5 eq of NMF, 1 mL).

Steps 3 and 4 from Method 2 were followed for polymer coating and purification.

Single Particle Tracking

Sample Preparation & Microscopy

NIR QDs prepared in 50 mM borate buffer were dispersed in glycerol to reach a final concentration of 0.123 nM and a glycerol concentration of ~97%. For imaging, ~100 μL of the QDs dispersed in the 97% glycerol solution were deposited on a #1.5 coverslip.

All samples were imaged using highly-inclined laminar optical sheet (HILO) microscopy on a Zeiss Axio Observer.Z1 inverted microscope (Zeiss, Oberkochen, Germany) with a 100×1.45 NA alpha Plan-Fluar oil immersion microscope objective and by use of a 100 W halogen lamp for fluorescence excitation. The particles were excited with a 488 nm laser line. Emission light was filtered by a 730/68 nm bandpass filter (Semrock Inc., Rochester, N.Y.). Data was acquired on a Photometrics eXcelon Evolve 512 EMCCD (Photometrics, Tuscon, Ariz.) and using Zeiss Zen software. All samples were uniformly excited and data was collected for 30 seconds at a rate of 21.64 frames/s.

Data Analysis

Single particle detection and tracking was done using the u-track MATLAB software package developed by Jaqaman and colleagues, Jaqaman et. al. Nat Methods 2008, 5; 689-702. Custom MATLAB scripts were used to calculate MSD values for all of the tracked particles and to fit a Brownian motion model to the first 4 time-lags in order to calculate diffusion coefficient values. In order to accurately calculate hydrodynamic diameters from these diffusion coefficient values, only particle tracks with a length of 200 frames or more (based on literature recommendations in Saxton et. al. J Biophys J 1997, 72; 1744-1753 and Ernst and Kohler, J. Phys. Chem. 2013 15; 845-849) and a diffusion coefficient greater than 0.02 $\mu m^2/s$ (based on the empirically determined localization error for immobilized particles on our system) were included in the hydrodynamic diameter calculations. Hydrodynamic diameters were calculated using the Stokes-Einstein relation and known viscosity values of glycerol solutions, see Segur and Oberstar, Ind. Eng. Chem. Res. 1951, 43; 2117-2120.

Instrumentation

Optical Spectroscopy and Fluorescence Quantum Yield (QY) Measurements

Fluorescent spectra were measured using a NanoLog Horiba Jobin Yvon (HORIBA Scientific, New Jersey, N.J., USA) and data were collected with Fluo Essence V3.5 software. UV-Vis spectra were obtained using a Cary series UV-Vis-NIR spectrophotometer (Agilent Technologies, Santa Clara, Calif., USA) and data were collected with Cary WinUV Scan Application Version 6.00 1551 software. For fluorescence QY measurements, the solution was diluted to give NPL absorption of ~0.1 at 490 nm. QY was calculated relative to a reference dye (fluorescein in 1 mM NaOH, QY=92%).

Transmission Electron Microscopy (TEM)

TEM images were obtained using a JEOL 2010 $LaB_6$ high-resolution microscope in the Frederick Seitz Materials Research Laboratory Central Research Facilities at University of Illinois. For QDs in organic solvents, samples were prepared by placing a drop of dilute NPL solution in hexane on an ultrathin carbon film TEM grid (Ted Pella; Product #01824) and then wick the solution off with a tissue.

$^1H$ and $^{13}C$ NMR $^1H$ and $^{13}C$ NMR spectra were recorded on a Varian U400 MHz, a UI500NB MHz or a VXR-500 MHz spectrometer.

Dynamic Light Scattering

Light-scattering analysis was performed on a Malvern Zetasizer (Herrenberg, Germany). The QDs samples were about 300 nM and filtered through a 0.2 μm filter (Catalog No. 28143-300, VWR). Each trace for autocorrelation was acquired for 15 s, and averaged over 11 runs per measurement. The autocorrelation function was analyzed using Zetasizer software (ver. 7.02, Malvern Instruments Ltd.). Each DLS measurement resulted in an average QD diameter with a standard error of the mean. Hydrodynamic diameters were obtained from a number-based distribution and reported as the mean±SEM of the triplicate measurements.

Zeta Potential

Zeta-potential of QDs were evaluated by a Malvern Zetasizer (Herrenberg, Germany). Zeta-potentials were measured in 10 mM phosphate buffer (pH 7.4) in a disposable capillary cell (DTS1070). Values were reported as the mean±SEM of triplicate measurements consisting of 20 scans.

Gel Permeation Chromatography (GPC) for QD Size Determination

GPC experiments for polymers were performed on a system equipped with an isocratic pump (Model 1100, Agilent Technology, Santa Clara, Calif., USA). The molecular weights of polymers were processed by the ASTRA V5.1.7.3.

Gel Electrophoresis

Gel electrophoresis was performed using an EPS-300X system (C.B.S. Scientific Company, Inc., Del Mar, Calif., USA) and gel images were acquired with a Gel Doc™ XR$^+$ System (Hercules, Calif., USA).

Gel Permeation Chromatography (GPC) for Polymer Analysis

GPC was performed on an ÄKTApurifier UPC10 (GE Healthcare, Umeå, Sweden) with a Superose™ 6 10/300GL column (GE Healthcare Bio-Sciences AB, Uppsala, Sweden) and data were processed with UNICORN 5.31 Workstation software.

Fluorescence Microscopy

Samples were imaged on a Zeiss Axio Observer Z1 inverted microscope. Hoechst signal was imaged using a 365 nm excitation filter and 445/50 nm emission filter; QD565 signal was imaged using a 488 nm laser excitation and a 562/40 bandpass emission filter; QD600 signal was imaged using a 488 nm laser excitation and a 600/37 bandpass emission filter. Images from the control and QD samples were collected using the same imaging condition.

The invention claimed is:

1. A method of making a quantum dot having a substantially homogeneous population of monomeric nanocrystals, the method comprising:
    coating a nanocrystal that is substantially free of hydrophobic ligands with weakly binding ligands or ions to form a nanocrystal coated with weakly binding ligands or ions;
    mixing the nanocrystal coated with weakly binding ligands or ions with at least one polymer in a solution, wherein the at least one polymer is a multidentate polymer selected from poly(N-acryloyloxysuccinimide) (PNAS) having a thiol (P-SH), PNAS having an imidazole (P-IM), PNAS having monoamine triethylene glycol (P-IM-N3), and combinations thereof;
    incubating at a temperature from 100° C. to 130° C. for 1 to 4 hours; and
    forming a quantum dot having a hydrodynamic diameter range of about 7 nm to about 12 nm, and a substantially homogeneous population of monomeric nanocrystals, wherein about 80% to about 100% of the monomeric nanocrystals fall within the hydrodynamic diameter range.

2. The method of claim 1, wherein the weakly binding ligands or ions are selected from weakly binding ions, the weakly binding ions being selected from $Cd^{2+}$, $Zn^{2+}$, $S^{2-}$, $Se^{2-}$, $Te^{2-}$, $OH^-$, $NH_2^-$, $SCN^-$, and $Cl^-$, and combinations thereof.

3. The method of claim 1, wherein the weakly binding ligands or ions are selected from weakly binding ligands, the weakly binding ligands being selected from mercaptoacetic acid, mercaptopropionic acid, mercaptoundecanoic acid, beta-mercaptoethanol, thioglycerol, mPEG-SH, and OH-PEG-SH, and combinations thereof.

4. The method of claim 1, wherein the solution is a polar solvent.

5. The method of claim 4, wherein the polar solvent is selected from dimethyl sulfoxide (DMSO), N-methylformamide (NMF), dimethylformamide (DMF), formamide, acetonitrile, N-methyl-2-pyrrolidone (NMP), ethanol, and methanol, and combinations thereof.

6. The method of claim 1, wherein the nanocrystal is selected from the group consisting of: $CdSe/Cd_xZn_{1-x}S$, CdSe/CdS, CdSe/ZnS, $Hg_xCd_{1-x}Se/Cd_yZn_{1-y}S$, or $CdSe_xS_{1-x}/Cd_yZn_{1-y}S$, and combinations thereof, wherein X and Y are each independently selected from a real number from zero to 1, inclusive.

7. The method of claim 1, further comprising conjugating a bioaffinity molecule to the quantum dot.

8. The method of claim 7, further comprising conjugating a bioaffinity molecule to the quantum dot using azide-alkyne click chemistry.

9. The method of claim 1, further comprising:
coupling the quantum dots with cyclooctynes under ambient conditions in an aqueous solvent to form a cyclooctyne coupled quantum dot; and
mixing the cyclooctyne coupled quantum dot with a cyclooctyne modified bioaffinity molecule, thereby attaching the bioaffinity molecule to the quantum dot.

10. The method of claim 7, further comprising conjugating a bioaffinity molecule to the quantum dot using self-assembly hexa-histidine-tagged proteins.

11. The method of claim 1, wherein the quantum dots having a substantially homogeneous population of monomeric nanocrystals are selected from quantum dots having a substantially homogeneous population of amine containing monomeric nanocrystals, and wherein the method further comprises mixing the quantum dots having a substantially homogeneous population of amine containing monomeric nanocrystals with a His-tagged bioaffinity molecule, thereby conjugating the His tagged bioaffinity molecule to the quantum dots.

* * * * *

SEQUENCE LISTING

```
<160> NUMBER OF SEQ ID NOS: 3

<210> SEQ ID NO 1
<211> LENGTH: 89
<212> TYPE: DNA
<213> ORGANISM: artificial sequence
<220> FEATURE:
<221> NAME/KEY: source
<223> OTHER INFORMATION: synthetic oligonucleotide
<220> FEATURE:
<221> NAME/KEY: modified_base
<222> LOCATION: (1) . . (1)
<223> OTHER INFORMATION: dibenzocyclooctyl-triethyleneglycol-T

<400> SEQUENCE: 1
tttttttttt tttttttttt tttttttttt tttttttttt tttttttttt tttttttttt      60 tttttttag ccagtgtatc gcaatgacg                                         89

<210> SEQ ID NO 2
<211> LENGTH: 21
<212> TYPE: DNA
<213> ORGANISM: artificial sequence
<220> FEATURE:
<221> NAME/KEY: source
<223> OTHER INFORMATION: synthetic oligonucleotide
<220> FEATURE:
<221> NAME/KEY: modified base
<222> LOCATION: (1) . . (1)
<223> OTHER INFORMATION: 6-fluorescein amidite-C

<400> SEQUENCE: 2
cgtcattgcg atacactggc t                                                21

<210> SEQ ID NO 3
<211> LENGTH: 89
<212> TYPE: DNA
<213> ORGANISM: artificial sequence
<220> FEATURE:
<221> NAME/KEY: source
<223> OTHER INFORMATION: synthetic oligonucleotide
<220> FEATURE:
<221> NAME/KEY: modified_base
<222> LOCATION: (1) . . (1)
<223> OTHER INFORMATION: biotin-T

<400> SEQUENCE: 3
tttttttttt tttttttttt tttttttttt tttttttttt tttttttttt tttttttttt      60
ttttttttta gccagtgtat cgcaatgac                                        89
```